United States Patent
Sintov

(10) Patent No.: US 11,246,934 B2
(45) Date of Patent: Feb. 15, 2022

(54) NANOPARTICLES AND METHODS FOR PREPARATION THEREOF

(71) Applicant: B.G. Negev Technologies & Applications Ltd. at Ben-Gurion University, Beer-Sheva (IL)

(72) Inventor: Amnon Sintov, Omer (IL)

(73) Assignee: B.G. NEGEV TECHNOLOGIES & APPLICATIONS LTD. AT BEN-GURION UNIVERSITY, Beer-Sheva (IL)

( * ) Notice: Subject to any disclaimer, the term of this patent is extended or adjusted under 35 U.S.C. 154(b) by 0 days.

(21) Appl. No.: 15/541,555

(22) PCT Filed: Jan. 5, 2016

(86) PCT No.: PCT/IL2016/050004
§ 371 (c)(1),
(2) Date: Jul. 5, 2017

(87) PCT Pub. No.: WO2016/110839
PCT Pub. Date: Jul. 14, 2016

(65) Prior Publication Data
US 2018/0104347 A1     Apr. 19, 2018

Related U.S. Application Data

(60) Provisional application No. 62/099,598, filed on Jan. 5, 2015.

(51) Int. Cl.
*A61K 47/32*     (2006.01)
*A61K 9/51*     (2006.01)

(52) U.S. Cl.
CPC ............ *A61K 47/32* (2013.01); *A61K 9/5115* (2013.01); *A61K 9/5138* (2013.01); *A61K 9/5153* (2013.01)

(58) Field of Classification Search
None
See application file for complete search history.

(56) References Cited

U.S. PATENT DOCUMENTS 5,989,535 A    11/1999   Nayak
7,674,767 B2 *   3/2010   Pai .................... A61K 38/28
                                                         514/1.1

(Continued)

FOREIGN PATENT DOCUMENTS

EP       1 943 016 B1    8/2012
WO      03033592 A1    4/2003

(Continued)

OTHER PUBLICATIONS

Deepa et al., "Cross-linked acrylic hydrogel for the controlled delivery of hydrophobic drugs in cancer therapy", International Journal of Nanomedicine, 2012, pp. 4077-4088. (Year: 2012).*

(Continued)

*Primary Examiner* — Kyung S Chang
(74) *Attorney, Agent, or Firm* — McCormick, Paulding & Huber PLLC

(57) ABSTRACT

The invention provides a nano-sized particle comprising a cross-linked polymer, wherein the polymer is selected from the group consisting of a polyacrylic acid homopolymer; polymethacrylic acid homopolymer; poly(alkylcyanoacrylate) polymer; a copolymer comprising at least two monomers selected from acrylic acid, methacrylic acid, hydroxyethyl acrylate, hydroxyethyl methacrylate, and alkyl cyanoacrylate/cyanoacrylic acid monomers; carboxymethyl cellulose; alginic acid polymer, polylactic-polyglycolic acid (PLGA), and xanthan gum; and wherein said polymer is cross-linked with a metal ion. A process for preparing such particles is also provided.

5 Claims, 15 Drawing Sheets

(56) References Cited

U.S. PATENT DOCUMENTS

Figure 1A:
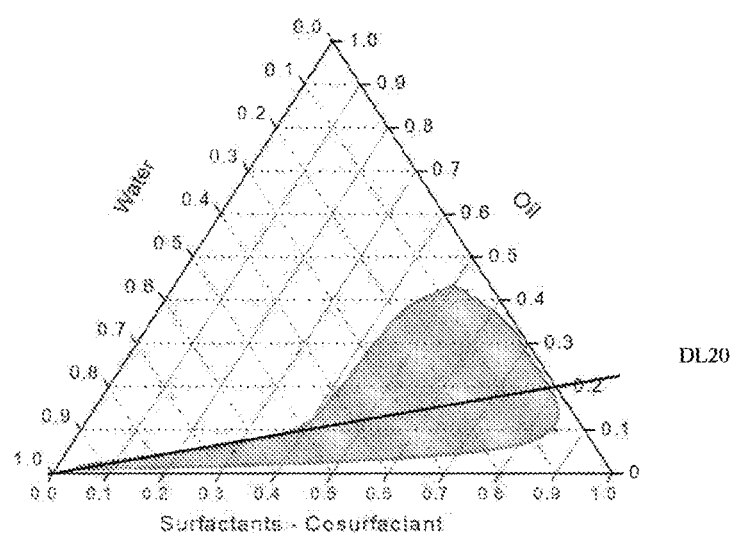

| | | |
|---|---|---|
| 2003/0177868 A1 | 9/2003 | Guillet |
| 2007/0251422 A1* | 11/2007 | Maenaka ............... C08G 18/30 106/287.28 |
| 2012/0107371 A1 | 5/2012 | Zion et al. |

FOREIGN PATENT DOCUMENTS

| | | | |
|---|---|---|---|
| WO | 2008/051432 A2 | 5/2008 | |
| WO | WO-2010069621 A * | 6/2010 | ........... A61K 9/0034 |
| WO | 2010074380 A1 | 7/2010 | |
| WO | 2014063662 A1 | 5/2014 | |

OTHER PUBLICATIONS

Burapapadh et al., "Development of pectin nanoparticles through mechanical homogenization for dissolution enhancement", Asian Journal of Pharmaceutical Science II (2016) pp. 365-375. (Year: 2016).*

Silverson Q & A of High shear mixer, [retrieved from on-line website: https://www.silverson.com/us/resource-library/high-shear-mixing-faqs/—access date: Feb. 25, 2021] (Year: 2021).*

International Search Report for PCT Serial No. PCT/IL2016/050004 dated Apr. 20, 2016.

Capek, Ignac, "Preparation of metal nanoparticles in water-in-oil (w/o) microemulsions", Advances in colloid and interface science, 2004, 110.1, Jun. 30, 2004, pp. 49-74.

Nagavarma, et al., "Different Techniques for Preparation of Polymeric Nanoparticles—A Review", Asian Journal of Pharmaceutical and Clinical Research, vol. 5, Suppl. 3, 2012, pp. 16-23.

Supplementary European Search Search Report for Serial No. EP 16 73 4955 dated May 15, 2018.

Nesamony et al., "Calcium Alginate Nanoparticles Synthesized Through a Novel Interfacial Cross-Linking Method as a Potential Protein Drug Delivery System," Journal of Pharmaceutical Sciences, vol. 101, p. 2177-2184 (2012).

Govender et al., "PLGA nanoparticles prepared by nanoprecipitation: drug loading and release studies of water soluble drug," Jounral of Controlled Release, vol. 57, p. 171-185 (1999).

Trotta et al., "Preparation of griseofulvin nanoparticles from water-durable microemulsions," International Journal of Pharmaceutics, vol. 254, p. 235-242 (2003).

Tewa-Tagne et al., "Spray-dried microparticles containing polymeric nanocapsules: Formulation aspects, liquid phase interactions and particles characteristics," International Journal of Pharmaceutics, vol. 325, p. 63-74 (2006).

Hsu et al., "Preparation and Characterization of Novel Coenzyme Q10 Nanoparticles Engineered from Microemulsion Precursors," AAPS PharmSciTech, vol. 4, No. 3, Article 32, p. 1-12 (2003).

Allemann et al., "In Vitro Extended-Release Properties of Drug-Loaded Poly(DL-Lactice Acid) Nanoparticles Produced by a Salting-Out Procedure," Pharmaceutical Research, vol. 10, No. 12, p. 1732-1737 (1993).

Chavanpatil et al., "Surfactant-polymer Nanoparticles: A Novel Platform for Sustained and Enhanced Cellular Delivery of Water-soluble Molecules," Pharmaceutical Research, vol. 24, No. 4, p. 803-810 (Apr. 2007).

Halder et al., "Chloramphenicol-incorporated poly lactide-co-glycolide (PLGA) nanoparticles: Formulation, characterization, technetium-99m labeling and biodistribution studies," Journal of Drug Targeting, vol. 16, No. 4, p. 311-320 (May 2008).

Lee et al., "Size control of self-assembled nanoparticles by an emulsion/solvent evaporation method," Colloid Polum Sci, p. 506-512 (2006).

Astete et al., "Synthesis and characterization of PLGA nanoparticles," Journal of Biomaterials Science, Polymer Edition , vol. 17, No. 3, p. 247-289 (2006).

Tewa-Tagne et al., "Spray-drying Nanocapsules in Presence of Colloidal Silica as Drying Auxiliary Agent: Formulation and Process Variables Optimization Using Experimental Designs," Pharmaceutical Research, vol. 24, No. 4, p. 650-661 (Apr. 2007).

You et al., "Calcium-Alginate Nanoparticles Formed by reverse Microemuslion as Gene Carriers," Macromol Symp., p. 147-153(2005).

"Molecular Weight of Carbopol® and Pemulen® Polymers," Lubrizol Technical Data Sheet, p. 1-3 (Oct. 15, 2007).

* cited by examiner

Fig. 2A
Fig. 2B
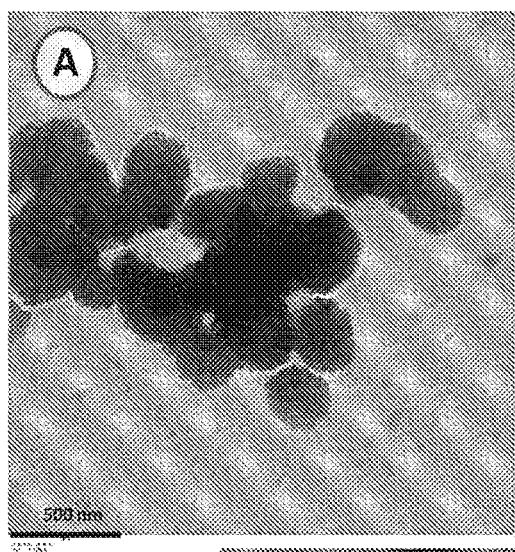
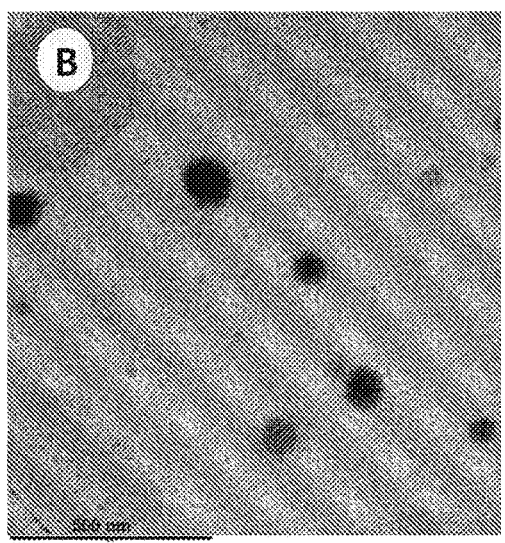
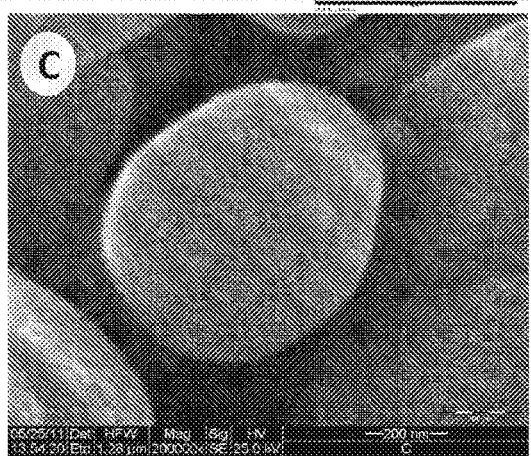
Fig. 2C

NANOPARTICLES AND METHODS FOR PREPARATION THEREOF

CROSS-REFERENCE TO RELATED APPLICATIONS

This application is a National Stage application of International Patent Application No. PCT/IL2016/050004, filed on Jan. 5, 2016, which claims priority to U.S. Patent Application No. 62/099,598, filed on Jan. 5, 2015, each of which is hereby incorporated by reference in its entirety.

BACKGROUND OF THE INVENTION

Nanotechnology is becoming increasingly more valuable in the fields of pharmaceutics and medical engineering, in which it offers exciting possibilities. This is due to the fact that particles made of nanoscale can more easily transport with their entrapped drug molecules through membranal barriers, thus increasing drug bioavailability. The controlled manner of drug release from the nanoparticles can prolong the therapeutic efficacy while reducing local and systemic adverse effects. One of the unmet needs for nanoparticles (NPs) is chloramphenicol (CHL). Topically-applied CHL is a widely used antibacterial drug in the form of eye drops for bacterial conjunctivitis. However, it has a low bioavailability (1-10%) and short half-life (1.5-5 h), thus needs to be applied many times a day [1, 2]. CHL is also applied in the vaginal treatment of local bacterial infections and can be a suitable candidate for prolonged therapy of vaginitis [3]. In addition, CHL is recommended by the World Health Organization (WHO) as the first line treatment of bacterial meningitis, although CHL may cause bone marrow suppression and aplastic anemia [4]. Several studies [4, 5, 6] have assessed the efficacy of intramuscular long-acting (oily suspension) CHL for bacterial meningitis and found it as a useful treatment. Another study using CHL formulation of polylactide-co-glycolide NPs has demonstrated a high brain uptake with relatively low accumulation of CHL in bone marrow, indicating the usefulness of NPs for controlled delivery of the drug [7].

Numerous methods have been applied to prepare polymeric NPs for drug delivery. These methods include: (a) emulsion/solvent evaporation (or emulsification-crosslinking) technology, in which evaporation of organic solvent (methylene chloride or chloroform) from an emulsion resulted in calcium-alginate NPs [8], or glycol chitosan NPs [9]; (b) nanoprecipitation from polymer-drug solution in water-miscible organic solvent upon slow introduction of surfactant-containing aqueous phase [10]; (c) salting-out method, in which a polymer-dissolved organic phase is emulsified in a saturated salt water under strong stress [11, 12]; (d) spray-drying procedure, in which dried nanoparticles are created in one-step process by atomization of polymer solution into a spray droplets that dried immediately as they contact hot air [13, 14], and (e) microemulsion as a precursor for NPs production [15-18].

EP 1943016 discloses composite NPs prepared by collapsing polymers such as polyacrylic acid, polystyrenesulfonic acid, and poly(diallyldimethylammonium chloride) from monophase solutions (aqueous or organic).

WO 2008051432 describes crosslinking effect by exposing a discrete portion of ionotropic polymer (e.g., polyacrylic acid) to a solution of an ionic species which exchanges with an ionic species in the polymer for production of patterned polymers.

Nagavarma et al., 2012 [22] summarizes the various techniques for preparation of NPs at the time of the present invention; nowadays, salting-out techniques are used with organic solvents for separation and without organic solvents for emulsification in order to "minimize stress to protein encapsulants".

Therefore, there is still an unmet need for a technique that would provide the formation of nanoparticles from common, physiologically acceptable polymers, such as polyacrylic/ methacrylic acid polymers, not known thus far to form stable, isolated nanoparticles that can carry drugs and other active agents, wherein the desired technique would not involve the use of organic solvents and/or other conditions that are not acceptable in the preparation of encapsulated drugs.

SUMMARY OF THE INVENTION

In was found in accordance with the present invention that when an aqueous solution of certain polymers having 50-70% free carboxylic acid groups or free amino groups, was added, in the presence of certain surfactants, to an oily phase, a water-in-oil microemulsion formed, from which self-assembled nanoparticles emerged by the addition of a cross-linking reagent to the microemulsion. By using the water-in-oil microemulsion as a reactor in the presence of a cross linking reagent, and combining the microemulsion with a salting-out/phase reversal process, a new method for producing nanoparticles was obtained. This method enabled formation of nanoparticles from polymers that were not previously known to assemble into well-defined particles.

The salting-out/phase reversal process used in accordance with the present invention eliminates the need to use organic solvents, such as acetone or alcohol, in any step of the process. The reactor microemulsion is prepared from pharmaceutically acceptable components, such as widely-used nonionic surfactants, and the aqueous polymer solution, for example a carbomer, e.g. Carbopol™ 974P solution, as the inner aqueous phase.

The involvement of microemulsions in NPs' mode of preparation is considered a novel composition apart of being a new process of manufacturing. Incorporation of surfactants and co-surfactants within a microemulsion (nano-sized emulsion) texture contributes to diminution and uniformity of NP size, to increasing of drug loading as well as to controlling of drug release, and certainly influences their physical properties. The instantly provided NPs are profoundly different from the particles known in the art. The particles known as "collapsed polymers" are formed by a phase separation of polymers in solution thereby converting the dissolved polymers into globules or other geometric shapes, having a wide distribution of particle sizes with various degrees of cross-linking that affect their properties. This undesired situation is avoided by using polymer-containing nanodroplets (microemulsions) that shape the desired morphology and geometrics of the NPs prior to the crosslinking step, as provided for by the present invention.

In an additional aspect, the polymeric nanoparticles of the present invention are slowly and controllably cross-linked with polyvalent cations, e.g. alkali earth cations. If calcium chloride solution is used, for example, precipitation of a lump is immediately generated. The cations may be supplied an organic acid salts of alkali earth metals with low degree of ionization. Additionally or alternatively, the cations may be supplied in a form of microemulsion, as described in greater detail below.

Therefore, in an aspect of the present invention a nano-sized particle comprising a cross-linked polymer, wherein the polymer is selected from the group consisting of a polyacrylic acid homopolymer; polymethacrylic acid homopolymer; poly(alkylcyanoacrylate) polymer; a copolymer comprising at least two monomers selected from acrylic acid, methacrylic acid, hydroxyethyl acrylate, hydroxyethyl methacrylate, alkyl cyanoacrylate and/or cyanoacrylic acid monomers; carboxymethyl cellulose; alginic acid polymer, polylactic-polyglycolic acid (PLGA), and xanthan gum; and wherein said polymer is cross-linked with a metal ion. The polymer may further be chemically cross-linked with a cross-linking moiety selected from the group consisting of allyl pentaerythritol, allyl sucrose, polyvinyl alcohol, divinyl glycol, and tetraethylene glycol. Sometimes, the polymer is a poly(acrylic acid), chemically cross-linked with allyl pentaerythritol or allyl sucrose. The metal ion may be a polyvalent metal ion selected from alkali earth metal ions, divalent transition metal ions, and trivalent metal ions, or Ag+. The alkali earth metal ion may be $Mg^{2+}$, $Ca^{2+}$, or $Sr^{2+}$. The particle may further comprise at least one active agent. The active agent may be selected from curcumin, an antineoplastic agent, selected from the group consisting of doxorubicin, carmustine, fluorouracil, cisplatin, cyclophosphamide, busulfan, carboplatin, leuprolide, megestrol, lomustine, levamisole, flutamide, etoposide, cytaranine, mitomycin, nitrogen mustard, paclitaxel, actinomycin, tamoxifen, vinblastine, vincristine, thiotepa, and chlorambucil, an antiinfective agent selected from the group consisting of interferons, acyclovir, valacyclovir, chloramphenicol, gentamycin, penicillin derivatives, streptomycin, aminoglycosides, cephalosporine, erythromycin and tetracycline. Particularly, the active agent is chloramphenicol, curcumin or doxorubicin. Sometimes the particle may have an essentially spherical shape and a size of 50-500 nm. In some particular embodiments, the particle may comprise poly(acrylic acid) cross-linked with allyl pentaerythritol or allyl sucrose, and the polyvalent metal ion may be $Ca^{2+}$.

In an additional aspect, provided is a composition comprising particles as disclosed herein in a physiologically acceptable carrier. The composition may be a pharmaceutical composition or a cosmetic composition.

In further aspect of the present invention, provided is a method for producing nano-sized particles, the method comprising the steps of combining together at least one oil, at least one surfactant and at least one co-surfactant, to form an oily mixture, adding a polymer containing carboxylic acid groups to water optionally in the presence of a base or a buffering agent, to form a polymer solution, combining together the oily mixture with the polymer solution to form a water-in-oil microemulsion, adding a metal ion source into said water-in-oil microemulsion, to form nano-sized particles, and recovering said nano-sized particles. The method may further comprise recovering the nano-sized particles by destabilizing the water-in-oil emulsion to allow phase separation, followed by collecting the nano-sized particles from the aqueous phase. Sometimes, the destabilizing is achieved by adding an aqueous salt solution into the water-in-oil microemulsion containing the nano-sized particles. The aqueous salt solution may comprise sodium chloride as the salt, and optionally a lyophilization additive or an osmolarity adjustment additive. Sometimes the collecting may be performed by extrusion through a filter membrane. In some embodiments, the metal ion source may be a salt selected from salts of alkali earth metals, salts of divalent transition metals, and salts of trivalent metals, or silver salts. Particularly, the salt may be $Mg^{2+}$, $Ca^{2+}$, or $Sr^{2+}$ salt. Usually the counter-ion in said metal salt is an organic acid. In some embodiments, the salt is calcium gluconate. The polymer may be selected from the group consisting of a polyacrylic acid homopolymer; polymethacrylic acid homopolymer; poly(alkylcyanoacrylate) polymer; a copolymer comprising at least two monomers selected from acrylic acid, methacrylic acid, hydroxyethyl acrylate, hydroxyethyl methacrylate, alkyl cyanoacrylate and/or cyanoacrylic acid monomers; carboxymethyl cellulose; alginic acid polymer; polylactic-polyglycolic acid (PLGA); and xanthan gum. The polymer may sometimes be chemically cross-linked with a cross-linking moiety selected from the group consisting of allyl pentaerythritol, allyl sucrose, polyvinyl alcohol, divinyl glycol, and tetraethylene glycol. In some embodiments, the method may further comprise adding an active agent to the microemulsion and/or to the aqueous polymer solution. The active agent may be selected from curcumin, a antineoplastic agent selected from the group consisting of doxorubicin, carmustine, fluorouracil, cisplatin, cyclophosphamide, busulfan, carboplatin, leuprolide, megestrol, lomustine, levamisole, flutamide, etoposide, cytaranine, mitomycin, nitrogen mustard, paclitaxel, actinomycin, tamoxifen, vinblastine, vincristine, thiotepa, and chlorambucil, an antiinfective agent selected from the group consisting of interferons, acyclovir, valacyclovir, chloramphenicol, gentamycin, penicillin derivatives, streptomycin, aminoglycosides, cephalosporine, erythromycin, and tetracycline. Sometimes the surfactant may be at least one of a non-ionic surfactants selected from the group consisting of capryloylcaproyl macrogol-8-glycerides (Labrasol), gelatin, albumin, starch, polyvinylpyrrolidone, polyvinyl alcohol, cetostearyl alcohol, glyceryl monoesters of fatty acids, polyglyceryl-6-dioleate, polyoxyethyleneglycol derivatives of fatty acids, polyoxyethyleneglycol ethers, polyoxyethylene alcohol ethers, polyoxyethylene sorbitan derivatives, sorbitan esters of fatty acids, and sugar esters. Sometimes the oil may be selected from the group consisting of isopropyl palmitate, isopropyl myristate, diethyl sebacate, diisopropyl adipate, cetyl oleate, oleyl alcohol, hexadecyl stearate, hexadecyl alcohol, caprylic triglycerides, capric triglycerides, isostearic triglycerides, adipic triglycerides, medium chain triglycerides, PEG-6-olive oil (Labrafil), esters of alkyl or monoglycerides, diglycerides and triglycerides of mono-, di- or tri-carboxylic acids, propylene glycol myristyl acetate, lanolin oil, polybutene, wheatgerm oil, vegetable oils, castor oil, corn oil, cottonseed oil, olive oil, palm oil, coconut oil, canola oil, sunflower oil, jojoba oil, peanut oil, hydrogenated vegetable oils, low water-soluble tertiary amides, ethoxylated fats, mineral oil, petrolatum, animal fats, and polyols. The co-surfactant may be selected from the group consisting of propylene carbonate, propylene glycol, tetraglycol (glycofurol), a polyethylene glycol, benzyl alcohol, propanol, and butanol. Particularly, the active agent may be chloramphenicol, curcumin or doxorubicin. More particularly, the polymer may be poly(acrylic acid) cross-linked with allyl pentaerythritol or allyl sucrose, and the polyvalent metal ion may be $Ca^{2+}$, and the organic acid salt may be gluconate.

DETAILED DESCRIPTION OF THE INVENTION

In one aspect, the present invention provides nano-sized particles comprising a polymer having 50-70% mole free carboxylic acid groups. Preferably, the polymer has not been known hitherto to form nanoparticles. The nanoparticles may further comprise at least one drug. Preferably, the polymer is a pharmaceutical-grade polymer.

The polymers particularly suitable for formation of the nanoparticles of the present invention include homopolymers of acrylic acid and methacrylic acid, copolymers comprising monomers of acrylic acid, methacrylic acid and/or their hydroxyalkyl, e.g. hydroxyethyl, monomers, copolymers comprising monomers of alkyl cyanoacrylate and/or acrylic/methacrylic acid/or cyanoacrylic acid, cellulose derivatives, e.g. carboxymethyl cellulose or xanthan gum, and alginic acid.

Sometimes, the polymer forming the nanoparticles is a cross linked polymer in itself. The cross-links may by a moiety selected from, but not limited to, a polyalkenyl polyether, allyl sucrose, polyvinyl alcohol, divinyl glycol, or tetraethylene glycol. In particular embodiments, the polymer, for example, a polyacrylic acid polymer or polymethacrylic acid polymer, is cross-linked with a polyalkenyl polyether moiety such as allyl ethers of pentaerythritols, or polyhydric alcohols containing more than one alkenyl group per molecule and at least 2 hydroxyl groups.

In certain embodiments, the nano-sized particles of the invention are formed from a cross-linked poly acrylic acid polymer (carbomer), preferably a polyacrylic acid polymer cross-linked with allyl pentaerythritol or allyl sucrose.

The term "carbomer" as used herein relates to a homopolymer of acrylic acid, which is cross-linked with any of several polyalcohol allyl ethers and/or polyalkenyl ethers. As used herein, "carbomer" also encompasses "carbopol", which is a polymer of acrylic acid cross-linked with polyalkenyl ethers or divinyl glycol. Carbomers are commonly used in stabilizing emulsions and providing viscosity to solutions. Carbopol® homopolymers are known as "carboxyvinyl polymers" and "carboxy polymethylene polymers". Examples of commercially available carbopols include the carboxy polymethylene Carbopol® 934P and the polyacrylic acid Carbopol® 980NF. Carbopol copolymers, such as Carbopol® 1342 NF and 1382, which are acrylates/Alkyl Acrylates cross polymers are also encompasses by the term "carbomer".

Carbopol polymers are manufactured, starting from primary polymer particles of about 0.2 to 6.0 micron average diameter, by a cross-linking process. Depending upon the degree of cross-linking and manufacturing conditions, various grades of Carbopol are available. Carbopol® 934P is cross-linked with allyl sucrose and is polymerized in solvent benzene. Carbopol® 71G, 971P, 974P are cross-linked with allyl penta erythritol and polymerized in ethyl acetate. Polycarbophil is cross-linked with divinyl glycol and polymerized in solvent benzene. Carbopol® 971P has slightly lower level of cross-linking agent than Carbopol® 974P although they are both manufactured by the same process under similar conditions. Carbopol 71G is the granular form Carbopol grade.

The polyalcohol portion gives a carbomer its high water solubility. Carbomers readily absorb water, get hydrated and swell. They are capable of absorbing large amounts of water, increasing in volume up to 1,000 times their original volume and 10 times their original diameter, and most often form a gel when exposed to a pH environment above 4.0 to 6.0. The carboxyl groups provided by the acrylic acid backbone of the polymer are responsible for many of the product benefits. Because the pKa of these polymers is 6.0 to 0.5, these carboxyl ionize, resulting in repulsion between the native charges, which adds to the swelling of the polymer. In some cases the swollen polymer chains form gels and thick solutions. The flocculated agglomerates and colloidal, mucilage-like dispersions formed when a carbomer absorbs water cannot be broken into the ultimate particles once it is produced, and can be viewed as a network structure of polymer chains interconnected via cross-linking. The readily water-swellable carbomer polymers are thus used in a diverse range of pharmaceutical applications mostly as excipients.

Preferably, the microemulsion has droplets size of between 5-50 nm.

The microemulsion reactor containing the (cross linked) polymer, for example carbomer, may be a coacervate formed by the coacervation process. The term "coacervation", as used herein, relates to a colloidal phenomenon, wherein a colloidal solution separates into two non-miscible parts, one richer in dispersed colloidal material than the other. The colloid-rich phase is called "the coacervate". The colloid-poor phase is called the equilibrium liquid and has a low or negligible content of colloidal material. In a coacervate, the distribution of colloid particles is statistically uniform, as in the original solution, although their concentration may be increased. In the water-in-oil microemulsion resulting from combining an oily mixture with an aqueous solution of a polymer, the spontaneously formed microdroplets of polymer solution may form coacervates.

The nano-sized particles provided by the present invention are soft, flexible particles having spherical shape and a size of 50-500 nm. Preferably, the particles have size of 100-400 nm, most preferably 200-300 nm, but sometimes the particles may be 50-200 nm, and preferably 50-100 nm.

The polymers suitable for the present invention may be cross-linked with a polyvalent cation. The cations suitable for the present invention are polyvalent cations. These include alkali earth cations, such as $Ca^{2+}$, $Mg^{2+}$ and $Sr^{2+}$; divalent transition metals cations, such as $Fe^{2+}$, $Mn^{2+}$, $Cu^{2+}$, $Mo^{2+}$ and $Zn^{2+}$; and trivalent cations, such as $Cr^{3+}$, $Au^{3+}$, $Fe^{3+}$, and $Al^{3+}$. Additionally or alternatively, the cation may form coordination bonds with structures in the polymer, e.g. with carbonyls, in addition to ionic interactions, e.g. transition metals' cations, and $Ag^+$ and $Au^+$.

The crosslinking ratio between the polyvalent cation and the polymer in the nanoparticle may be adjusted to achieve the desired amount of cross-links. Usually, the cross-linking ratio is between 0.01 to 0.5 of cation ion weight per polymer weight, and more preferably between 1:10 to 1:1. Sometimes, the crosslinking ratio may be provided as percentage of equivalents, taking into account the polyvalent nature of the cations. In such cases, the cross-linking ratio may be from 0.01 to 0.1, and preferably between 1:10 to 1:2.

The nano-sized particles of the invention are suitable as a platform for carrying at least one active agent. The active agent may be encapsulated within the nano-sized particle, non-covalently associated thereto, ionically or electrically associated thereto, and/or embedded or incorporated in the nano-sized particle matrix.

In certain embodiments, the active agent is encapsulated within the nano-sized particle as a well-defined core inside the nanoparticle, or as a gradient from inside to the boundary of said nanoparticle.

In certain other embodiments, the active agent is embedded within the nano-sized particle matrix either homogeneously by being uniformly dissolved in the polymer matrix, or heterogeneously by being dispersed as clusters or aggregates in the polymer matrix.

Any active agent may be delivered or carried by the nanoparticles of the invention. Particular classes of active agents include, but are not limited to, biologically active agents, radioactive labels, diagnostic markers, cosmetic or cosmeceutic agents, nutrition or naturaceutic agents, as well contrast agents for imaging procedures.

Non-limiting examples of biologically active agents in the nano-sized particles include curcumin, antineoplastic agents, such as doxorubicin, carmustine, fluorouracil, cisplatin, cyclophosphamide, busulfan, carboplatin, leuprolide, megestrol, lomustine, levamisole, flutamide, etoposide, cytaranine, mitomycin, nitrogen mustard, paclitaxel, actinomycin, tamoxifen, vinblastine, vincristine, thiotepa, chlorambucil, antiinfective (e.g. antiviral or antibacterial) agents such as interferons (e.g., alpha2a,b-interferon, beta-interferon), acyclovir, valacyclovir, chloramphenicol, gentamycin, penicillin derivatives, streptomycin, aminoglycosides, cephalosporine, erythromycin and tetracycline.

In certain embodiments, the present invention provides nano-sized particles loaded with chloramphenicol, curcumin, or doxorubicin (also known as Adriamycin). From the pharmacology standpoint, the nanoparticles of the present invention fulfill the requirements of ideal drug delivery systems: ease and reproducibility of preparation, ease of storage and administration in a sterile form, satisfying drug-loading capacity, low toxicity, and feasibility for scale-up production. By varying one or more experimental parameters (polyvalent ions and their quantities, polymer concentration, water content, surfactants ratio, etc.), various types of nanoparticles can be obtained, each exhibiting specific features regarding the nature of the drug and the way it is encapsulated.

In particular embodiments, the chloramphenicol-containing nano-sized particles, or the curcumin-containing nano-sized particles of the invention are comprised of a cross-linked polyacrylic acid polymer (carbomer). In more particular embodiments, the carbomer is polyacrylic acid cross-linked with allyl pentaerythriol or allyl sucrose.

The nano-sized particles of the invention may further comprise at least one additive for targeting purposes, for enhancing permeability and/or for increasing the stability of the nano-sized particle. Non-limiting examples of additives for nanoparticle targeting include paramagnetic moieties such as iron oxide. Magnetic targeting combined with ultrasound directed to the diseased area (tumor, infection, or inflammation) can mediate a more effective and safer drug delivery.

In another aspect, the present invention provides a composition comprising the nano-sized particles of the invention and a physiologically acceptable carrier. In certain embodiments, the composition is a pharmaceutical composition. In certain other embodiments, the composition is a cosmetic composition.

In a further aspect, the present invention provides a method for producing nano-sized particles, the method comprising the steps of combining together at least one oil, at least one surfactant and at least one co-surfactant, to form an oily mixture, adding a polymer containing carboxylic acid groups to water optionally in the presence of a base or a buffering agent, to form a polymer solution, combining together the oily mixture with the polymer solution to form a water-in-oil microemulsion, adding a metal ion source into said water-in-oil microemulsion, to form nano-sized particles, and recovering said nano-sized particles. The method may further comprise recovering the nano-sized particles by destabilizing the water-in-oil emulsion to allow phase separation, followed by collecting the nano-sized particles from the aqueous phase. Sometimes, the destabilizing is achieved by adding an aqueous salt solution into the water-in-oil microemulsion containing the nano-sized particles.

Preferably, the collecting of the nanoparticles is performed by extrusion through a filter membrane of suitable pore size, e.g. 100-200 nm pore size.

The method of the present invention may further comprise at least one step of:
a. adding the active agent, optionally dissolved in an aqueous solution, to the microemulsion and/or to the aqueous polymer solution;
b. providing the cross-linking reagent in a microemulsion of the part of the oily mixture and water.

Non-limiting examples of the active agents for use in the method include curcumin, antineoplastic agents, such as doxorubicin, carmustine, fluorouracil, cisplatin, cyclophosphamide, busulfan, carboplatin, leuprolide, megestrol, lomustine, levamisole, flutamide, etoposide, cytaranine, mitomycin, nitrogen mustard, paclitaxel, actinomycin, tamoxifen, vinblastine, vincristine, thiotepa, chlorambucil, antiinfective (e.g. antiviral or antibacterial) agents such as interferons (e.g., alpha2a,b-interferon, beta-interferon), acyclovir, valacyclovir, chloramphenicol, gentamycin, penicillin derivatives, streptomycin, aminoglycosides, cephalosporine, erythromycin and tetracycline.

In certain embodiments, the polymers used in the method of the invention are polymers containing 50 to 70% mol free carboxylic acid groups. In preferred embodiments, the polymers are selected from cross-linked polymers of acrylic acid and/or methacrylic acid, alginic acid polymers, xanthan gum, polymers of lactic acid and/or glycolic acid. In particular embodiments, the polymer is a cross-linked polymer of acrylic acid and/or methacrylic acid as defined above.

In certain other embodiments, the polymers used in the method of the invention are polymers containing free amino groups. In preferred embodiments, the polymers are selected from cationized guar gums or polyquaternium polymers.

In those embodiments wherein the method of the invention is utilized for the production of nanoparticles of polymers with high content of free amino groups, the cross linking reagent most preferably employed is a carboxylic acid compound such as citric acid, boric acid, or phosphoric acid, preferably citric acid.

The oil employed in the method provided herein is selected from at least one of isopropyl palmitate, isopropyl myristate, diethyl sebacate, diisopropyl adipate, cetyl oleate, oleyl alcohol, hexadecyl stearate, hexadecyl alcohol, caprylic triglycerides, capric triglycerides, isostearic triglycerides, adipic triglycerides, medium chain triglycerides ($C_8$-$C_{10}$ fatty acids), PEG-6-olive oil (Labrafil), esters of alkyl or monoglycerides, diglycerides and triglycerides of mono-, di- or tri-carboxylic acids, propylene glycol myristyl acetate, lanolin oil, polybutene, wheatgerm oil, vegetable oils such as castor oil, corn oil, cottonseed oil, olive oil, palm oil, coconut oil, canola oil, sunflower oil, jojoba oil, peanut oil, and hydrogenated vegetable oils, low water-soluble tertiary amides, ethoxylated fats, mineral oil, petrolatum, animal fats, and polyols. The preferred oil is isopropyl palmitate or isopropyl myristate.

The surfactants employed in the method of the invention are preferably non-ionic surfactants such as, but not limited to, at least one of capryloylcaproyl macrogol-8-glycerides (Labrasol), gelatin, albumin, starch, polyvinylpyrrolidone, polyvinyl alcohol, cetostearyl alcohol, glyceryl monoesters of fatty acids (e.g., glyceryl monostearate, glyceryl monooleate, or glyceryl dioleate), polyglyceryl-6-dioleate (Plurol oleique), polyoxyethyleneglycol derivatives of fatty acids (e.g., Myrj 45, 49, 51, 52, 52S, 53, 59), polyoxyethyleneglycol ethers (e.g., polyoxyethylene (23) dodecyl ether or Brij 35), polyoxyethylene alcohol ethers, polyoxyethylene sorbitan derivatives (polysorbates, e.g., Tweens such as Tween 20, 40, 60, 80, 85), sorbitan esters of fatty acids (e.g., sorbitan sesquioleate, sorbitan isostearate, sorbitan monolaurate, sorbitan monostearate, sorbitan monooleate), and sugar esters (e.g., Sisterna sucrose esters, which are based on sucrose and vegetable fatty acids). In some embodiments, at least two surfactants are used in the preparation of the oily mixture. The preferred surfactants are capryloylcaproyl macrogol-8-glycerides (Labrasol) and glyceryl monoesters of fatty acids.

The suitable co-surfactants for the method of the present invention are selected from at least one of propylene carbonate, propylene glycol, alkanols, e.g. propanol or butanol, benzyl alcohol, tetraglycol (glycofurol), and polyethylene glycol.

The ratio between the co-surfactants and the surfactants may be between 0.1 and 0.9, preferably between 0.2 and 0.6.

The polymer is dissolved in water to furnish polymeric solution. The polymeric solution may contain from 0.001% wt of polymer to about 0.5% wt, preferably from 0.01% wt to 0.05% wt.

Bases or buffering agents may be used in the preparation of the polymer solution for the method of the present invention. These include, but not limited to, alkali hydroxides, e.g. sodium or potassium hydroxide, ammonium hydroxide, suitable amines, e.g. triethyl amine, and triethanolamine.

Combining of the oily mixture with the polymer solution results in a spontaneous formation of the microemulsion. The combining may be performed at any suitable temperature, e.g. at room temperature, from about 15° C. to about 30° C., but may also be performed from 0° C. to 100° C., preferably about 30° C.

Cross-linking agent is added to the formed microemulsion to effect cross-linking. The cross-linking agent may usually be a polyvalent cation as described herein. The polyvalent cation is usually supplied in a form of a salt, preferably a salt of an organic acid that dissociates slowly in water. The cation counter-ions may be a saccharidic acid ion, e.g. gluconate, picolinic acid ion, or an aliphatic acid ion. Generally, the counter-ion may have a $pK_a$ of between 2 and 7. Preferably, the counter-ion is gluconate. Most preferably, the cross-linking agent is calcium gluconate.

Sometimes, the cross-linking agent may be provided as a microemulsion. The microemulsion may preferably contain similar or same composition of the oily mixture that the polymer water-in-oil microemulsion. The aqueous phase naturally comprises the cross-linking agent in aqueous solution, as disclosed herein.

Combining the cross-linking agent with the microemulsion requires a meticulous control over the addition rate of the cross-linking agent. Usually the addition rate is selected to prevent polymer precipitation as a lump, and may be selected from 0.001 mL/min/mL of microemulsion, to 0.5 mL/min/mL of microemulsion, more preferably 0.03 mL/min/mL of microemulsion.

The cross-linked nano-particles may be allowed to maturate for 5-30 minutes.

The nanoparticles are extracted into aqueous medium from the microemulsion by reversing the phase of the emulsion. Adding sufficient amount of aqueous phase causes phase separation and extracts the nanoparticles into the aqueous phase. Usually, the additional aqueous phase is added in amount of about 1:1 with the microemulsion, and may be between 1:2 and 2:1, preferably 1:1.

The aqueous solution for phase reversal usually contains salts, e.g. sodium chloride, or any water soluble salt, e.g. KCl, $NaHCO_3$, $Na_3PO_4$, $NaH_2PO_4$, and $Na2HPO4$. The salts may be in the amount varying from 0.5% wt to 10% wt; preferably the salt is sodium chloride and the concentration is between 3-6%. The aqueous solution may further comprise at least one additive. The additive may be used in further processing of the nanoparticles, such as lyophilization, or may be a part of the pharmaceutical composition. Such additives include, but not limited to, mannitol, and lactose. The additives may be employed in concentrations between 0.01 and 1%, preferably 0.1%.

Upon addition of the aqueous solution the phase separation will occur. The phase separation may take from 15 minutes to 4-12 hours, and may be performed at 25° C. to 50° C., preferably between 15° C. and 35° C. The phase separation may also be assisted by instrumental means, such as centrifugation, elevated or reduced pressure. In this case the phase separation may take less time.

Collecting of the obtained nanoparticles may be performed by a variety of methods, e.g. centrifugation, filtration through a filter of a suitable size, dialysis and others as known in the art.

The active agent used in the method of the invention may be any of the aforementioned active agents, namely, a biologically active agent, a radioactive label, a contrast agent, diagnostic marker, a cosmetic or cosmeceutic agent, a nutrition or naturaceutic agent. The active agent may be encapsulated within the nano-sized particle, non-covalently associated thereto, ionically or electrically associated thereto, and/or embedded or incorporated in the nano-sized particle matrix, preferably encapsulated within the nano-sized particle as a well-defined core inside the nanoparticle or as a gradient from inside to the boundary of said nanoparticle. When embedded within the nano-sized particle matrix, the active agent may either be uniformly dissolved in the polymer matrix (homogeneously embedded) or dispersed as clusters or aggregates in the polymer matrix (heterogeneously embedded).

In certain embodiments, nano-sized particles containing chloramphenicol, doxorubicin or curcumin are obtained by the method of the invention. In preferred embodiments, these nano-sized particles comprise a cross-linked polyacrylic acid polymer, preferably an allyl pentaerythriol-cross-linked polyacrylic acid polymer (a carbomer), and are formed by the use of the cross-linking reagent calcium gluconate.

EXAMPLES

Materials and Methods

1. Materials

Isopropyl palmitate, propylene carbonate and calcium gluconate were purchased from Aldrich (Sigma-Aldrich Inc., St. Louis, Mo.). Glyceryl oleate was obtained from Uniqema, Bromborough Pool, The Wirral, UK. Labrasol was obtained from Gattefosse, France. Carbopol®974P NF Polymer was obtained from Lubrizol, Ohio, USA. High-performance liquid chromatography (HPLC) grade solvents were obtained from J.T. Baker (Mallinckrodt Baker, Inc., Phillipsburg, N.J.). Chloramphenicol was obtained from Sigma, Rehovot, Israel. Curcumin was obtained from Sigma, Rehovot, Israel. Doxorubicin was obtained from Euroasian Chemicals Pvt. Ltd. (Mumbai, India).

2. NPs Preparation

Generally, microemulsions were prepared by mixing Labrasol, glyceryl oleate (surfactants) and isopropyl palmitate (oil) with propylene carbonate (co-surfactant). The co-surfactant to surfactants (CoS/S) weight ratio was 1:5, and the surfactants' ratio was 1:3. Appropriate volumes of Carbopol® 974P NF solution (pH=7) were solubilized along a dilution line—DL20, (DL20 means a line representing a surfactants-to-oil ratio of 80:20) (FIG. 1A). Formulations prepared along DL20 contained 0.01 wt % polymer in the microemulsion, and this concentration was kept constant regardless of changing in water content. The monophasic formulations were formed spontaneously at room temperature. After the microemulsion had been loaded with CHL and a clear liquid was obtained, an aqueous solution of calcium gluconate was added. To examine the calcium effect on NP size, several calcium gluconate levels were introduced into microemulsions to make up a total water phase of 25% (and 0.01% polymer concentration) at the following concentrations: 0.043%, 0.086%, 0.129%, 0.258%, and 0.430%.

The addition of calcium gluconate was performed by using a peristaltic pump operated at a controlled rate of 0.3 ml/min while microemulsions were kept at 35° C. under continuous stirring (300 rpm).

Figure 1B:
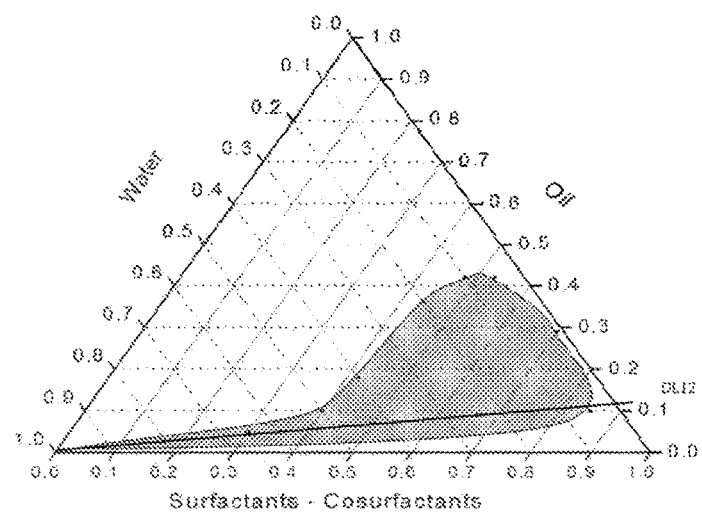

Turning now to FIGS. 1A and 1B, pseudo-ternary phase diagram represents a microemulsion system (shaded area) made of isopropyl palmitate (oil), glyceryl oleate and Labrasol (as surfactants at a 1:3 w/w ratio), propylene carbonate (co-surfactant) and water. The co-surfactant/surfactants ratio was 1:5. Lines DL20 and DL12 represent water dilution line at a constant surfactant-to-oil ratio of 4 (w/w) and 88:12, respectively.

Similarly, the microemulsion was prepared by mixing Labrasol, glyceryl oleate (surfactants) and isopropyl palmitate (oil) with propylene carbonate (co-surfactant) [20]. The co-surfactant to surfactants (CoS/S) weight ratio was 1:5, and the surfactants' ratio was 1:3. Appropriate volumes of Carbopol®974P NF solution (pH=7) were solubilized along a dilution line—DL12, (DL12 means a line representing a surfactants-to-oil ratio of 88:12) (FIG. 1B). Formulations prepared along DL12 usually contained 0.01 wt % polymer in the microemulsion, and this concentration was kept constant regardless of water content. The pH 7.5 was adjusted by a 0.5% triethanolamine solution. The monophasic formulations were formed spontaneously at room temperature. After the microemulsion had been loaded with 400 µg/ml doxorubicin and a clear colored liquid was obtained, an aqueous solution of calcium gluconate was added under constant stirring (1200 rpm) using a 10-ml syringe pump operated at a controlled rate of 0.3 ml/min at a temperature range of 25° C.-35° C. To examine the cross-linking effect of calcium ions on NP size and release, several calcium gluconate concentrations were introduced into the microemulsion (16% w/w of total aqueous phase, and 0.01% polymer concentration were kept constant) at the following Ca++ ions/polymer ratios: 1:10, 3:10, 1:2, and 1:1, as described below. To examine the effect of polymer concentrations on the size and release of the resulted NPs, three concentrations were prepared—0.01, 0.02, and 0.04%—while the Ca++ ions/polymer ratio (3:10) and the microemulsion's aqueous phase (16%) were kept constant. To examine the effect of the aqueous phase in the microemulsion on the NPs, formulations containing 16%, 20% and 25% aqueous phase were prepared, while the polymer concentration and the Ca++ ions/polymer ratio were kept constant.

3. Salting-Out and Separation of NPs

A solution containing 0.9% (w/v) sodium chloride was mixed gently with the calcified microemulsion at a 1:1 ratio, and the mixture was poured into a burette and allowed to separate for 12 hours. Two phases with different densities were obtained. The lower phase, a clear aqueous fluid containing the drug-loaded NPs in dispersion, was collected and extruded through a membrane of 200 nm (in diameter) pore size using Avanti Mini-Extruder (Avanti Polar Lipids Inc, Alabama, USA).

4. Size and Microscopic Analysis 4.1 Dynamic Light Scattering (DLS)

The hydrodynamic diameter spectrum of the NPs was collected using CGS-3 Compact Goniometer System (ALV GmbH, Langen, Germany). The laser power was 20 mW at the He-Ne laser line (632.8 nm). Correlograms were calculated by ALV/LSE 5003 correlator, which were collected at 60°, during 10 s for 20 times, at 25° C. The NP size was calculated using the Stokes-Einstein relationship, and the analysis was based on regularization method as described by Provencher [19].

4.2 Scanning Electron Microscopy (SEM)

The surface morphology of the NPs was inspected by scanning electron microscopy (SEM, JEOL JSM-35CF). The NP dispersion was first lyophilized and then coated with an ultrathin (100 Å) layer of gold in a Polaron E5100 coating apparatus. The samples were viewed under SEM at an accelerating voltage of 25 kV.

4.3 Transmission Electron Microscopy (TEM)

TEM images were recorded on a JEOL JEM-1230 transmission electron microscope (JEOL LTD, Tokyo, Japan) operating at 120 kV. Samples of NP dispersions were deposited on a copper 300 mesh grid, coated with Formvar and carbon (Electron Microscopy Sciences, Fort Washington, Pa., USA) and allowed to stand for 1 minute after which any excess fluid was adsorbed in a filter paper. Subsequently, one drop of 1% phosphotungstic acid (PTA) solution was applied on the grid and allowed to dry for 1 minute. Electron micrographs were taken using TemCam-F214 (Tietz Video & Image Processing Systems (TVIPS), Gauting, Germany).

5. Determination of Drugs in NP Dispersion 5.1. Chloramphenicol

Aliquots of 20 ml from each sample were injected into a HPLC system, equipped with a prepacked column (Luna C18 column, 5 µm, 150 mm×4.6 mm, Phenomenex, Torrance, Calif.). The HPLC system (Shimadzu VP series) consisted of an auto-sampler and a diode array detector. The quantification of chloramphenicol was carried out at 275 nm. The samples were chromatographed using an isocratic mobile phase consisting of acetonitrile-phosphate buffer, pH 5 (30:70) at a flow rate of 1 ml/min.

The drug concentration in the NP dispersion (lower phase) was estimated according to the following equation:

$$C_{dis} = \frac{Q_T - W_{up} * C_{up}}{W_{low}}$$

where $Q_T$ is the total amount of the drug dissolved in the microemulsion, $W_{up}$ and $W_{low}$ are the weights of the upper and lower phases, respectively and $C_{up}$ is the concentration of the drug in the upper phase (wt/wt).

5.1. Curcumin

Aliquots of 20 µL from each sample were injected into a HPLC system, equipped with a prepacked column (Reprosil-Pur 300 ODS-3, 5 um, 250 mm×4.6 mm, Dr. Maisch, Germany) which was constantly maintained at 30° C. The HPLC system (Shimadzu VP series) consisted of an auto-sampler and a diode array detector. The quantification of curcumin was carried out at 425 nm. The samples were chromatographed using a mobile phase consisting of acetonitrile-35 mM acetic acid (80:20) at a flow rate of 1 ml/min. A calibration curve (peak area vs. curcumin concentration) was constructed by running standard curcumin solutions in methanol. The calibration curves were linear over the range 0.025-10 μg/ml (r>0.99).

5.3. Doxorubicin

Aliquots of 20 μl were injected into a HPLC system, equipped with a prepacked column (ReproSil-Pur 300 ODS-3, 5 μm, 150 mm×4.6 mm, Dr. Maisch, Germany), which was constantly maintained at 30° C. The HPLC system (Shimadzu VP series) consisted of an auto-injector and a photodiode array detector. The quantification of DOX was carried out at 234 nm. The samples were chromatographed using an isocratic mobile phase consisting of acetonitrile-0.2% heptanesulfonic solution (40:60) at a flow rate of 1 ml/min.

6. Drug Release Studies

The amount of drug released from the NPs was determined by a dynamic dialysis technique monitoring the drug concentration in the receiver solution (i.e., outer solution surrounding a dialysis bag). The method is based on the assumption that drug is first released from the NPs into the donor solution (i.e., the dissolution medium inside the dialysis bag). Subsequently, the drug can diffuse through the dialysis bag from the donor to the receiver.

A sample of 3 ml of the NP dispersion (1:1 diluted with saline) was introduced into a dialysis bag (SnakeSkin Dialysis Tubing, 10K MWCO, 22 mm, Thermo Fisher Scientific, Rockford, USA). The sample was dialyzed against 60 ml of saline solution (NaCl solution, 0.9%, w/v) for 7 hours. The receiver solution was agitated by magnetic stirring throughout the experimental procedure. Samples of 200 μl were withdrawn from the receiver solution at predetermined time intervals and their drug concentrations were measured by HPLC.

Example 1: Production and Isolation of Calcium-Carbopol Nanoparticles

Self-assembled polymeric NPs were engineered by using a water-in-oil microemulsion template containing water-soluble polymer in the inner aqueous phase. The polymer (Carbopol 974P) in the nanodroplets was crosslinked by $Ca^{+2}$ ions to form NPs which were separated by simple and direct salting-out. Production of NPs by salting-out was previously described [E. Allémann, J. C. Leroux, R. Gurny, E. Doelker, In vitro extended-release properties of drug-loaded poly(DL-lactic acid) nanoparticles produced by a salting-out procedure, Pharm. Res. 10 (1993) 1732-1737] for poly(DL-lactic acid) NPs. In this publication, the polymer was dissolved in an organic phase (acetone), which should be miscible in all proportions with pure water but being separated and emulsified in salt-containing water. According to this method, NPs were generated upon gradual dilution of the emulsion to create a monophasic system. We utilized this method for calcium-Carbomer NP production, however, we have employed the salting-out technique for separation of NPs from the microemulsion oily components rather than for generation of NPs. This salting-out technique has been utilized in this research to avoid separation and washing of NPs by organic solvents.

Specific Example 1.1—Neat Calcium-Carbomer Nanoparticles

More specifically, the process was performed as follows.

An oil phase was produced by mixing together isopropyl palmitate, 6.0 g; glyceryl oleate, 9.25 g; Labrasol, 27.75 g; and propylene carbonate, 7.4 g; to furnish 50.4 g of the oil phase. The materials were combined in a beaker and mixed until dissolution, at ambient temperature. The co-surfactant to surfactants (CoS/S) weight ratio was preserved 1:5.

Carbomer aqueous solution was prepared by dispersing 0.05 g of Carbopol 974NF in 10 g of double-distilled water and mixing at room temperature until homogeneous mucilage was obtained, for about 5-10 minutes. Thereafter, sodium hydroxide solution was used to adjust the pH, about 50 μL, and the solution was stirred for additional 10 minutes. The solution contained 0.5% wt of polymer.

Microemulsion was prepared by mixing in a beaker 8.5 g of the oil phase with 0.2 g of polymer solution and 0.8 g of water, at room temperature. The water-in-oil microemulsion with 15% of aqueous phase and 0.01% wt of polymer was spontaneously formed.

Crosslinking was performed at 35° C. by adding 0.5 g of calcium gluconate solution, 0.645% wt in water, into the vigorously stirred microemulsion (300 rpm), using a peristaltic pump operated at a controlled rate of 0.3 ml/min. The obtained nanodispersion was stirred for additional 15 minutes.

The nanoparticles were separated from the microemulsion by diluting the bulk with 10 mL of wash solution containing 6% wt of sodium chloride and 0.5% wt of mannitol. The obtained mixture was allowed to separate in a burette for 4 hours or left overnight, and the bottom aqueous phase containing the nanoparticles was removed.

Specific Examples 1.2-1.9—Calcium-Carbomer Nanoparticles, Different Variables

Various nanoparticles were prepared based on the process of the Example 1.1. The formulations are shown in the table 1 below. IPP is isopropyl palmitate; 51 is glyceryl oleate; 51 is Labrasol; Co—S is propylene carbonate; Carbomer is Carbopol 974NF; CG is calcium gluconate aqueous solution; DDW is double-distilled water; and AqC is aqueous content.

TABLE 1

| | | | | Aqueous phase | | | |
|---|---|---|---|---|---|---|---|
| | | Surfactants | | Carbomer | CG, | | |
| Oil IPP, g | $S_1$, g | $S_2$, g | Co—S, g | 0.25% (w/w), g | DDW, g | % (w/w) | AqC wt. % |
| 1.2 | 1.125 | 1.64 | 4.922 | 1.312 | 0.4 | 0.1 | 0.645 | 10 |
| 1.3 | 1.06 | 1.55 | 4.65 | 1.24 | 0.4 | 0.6 | 0.645 | 15 |
| 1.4 | 1 | 1.458 | 4.375 | 1.167 | 0.4 | 1.1 | 0.645 | 20 |
| 1.5 | 1 | 1.458 | 4.375 | 1.167 | 0.4 | 1.1 | 0.215 | 20 |
| 1.6 | 1 | 1.458 | 4.375 | 1.167 | 0.4 | 1.1 | 0.429 | 20 |
| 1.7 | 1 | 1.458 | 4.375 | 1.167 | 0.4 | 1.1 | 1.074 | 20 |
| 1.8 | 1 | 1.458 | 4.375 | 1.167 | 0.24 | 1.26 | 0.387 | 20 |
| 1.9 | 1 | 1.458 | 4.375 | 1.167 | 0.56 | 0.94 | 0.902 | 20 |

Formulations 1.2-1.4 demonstrate microemulsions with different aqueous contents (10, 15, and 20% wt). Formulations 1.4-1.7 demonstrate microemulsions with 20% wt aqueous contents and different $Ca^{+2}$/Carbomer ratios (i.e. 1:10, 2:10, 3:10, 5:10). Formulations 1.4, 1.8 and 1.9 demonstrate microemulsions with 20% wt aqueous content, $Ca^{+2}$/Carbomer ratio of 3:10 with different polymer concentrations (i.e. 0.03, 0.05, 0.07 wt).

Specific Examples 1.10-1.19—Chloramphenicol-Loaded Nanoparticles

Chloramphenicol-loaded nanoparticles were prepared similarly. Specifically, the microemulsion was formed as in Example 1.1, and chloramphenicol, 0.5 g, was added into the microemulsion to final concentration 5% wt, and stirred at 1200 rpm for 10 minutes. Crosslinking was performed as in Example 1.1. The parameters are summarized in the Tables 2 and 3 below.

TABLE 2

|  | 1.10 | 1.11 | 1.12 | 1.13 | 1.14 |
|---|---|---|---|---|---|
| C carbomer in water | 0.2 wt % | 0.1 wt % | 0.067 wt % | 0.05 wt % | 0.04 wt % |
| C water in ME | 6.25% | 12.5% | 18.75% | 25% | 31.25% |
| C carbomer in ME | 1.25 wt % | 1.25 wt % | 1.25 wt % | 1.25 wt % | 1.25 wt % |

TABLE 3

|  | 1.15 | 1.16 | 1.17 | 1.18 | 1.19 |
|---|---|---|---|---|---|
| C $Ca^{+2}$/solution | 0.215 wt % | 0.43 wt % | 0.645 wt % | 1.29 wt % | 2.15 wt % |
| C $Ca^{+2}$ solution/ME | 20% | 20% | 20% | 20% | 20% |
| C $Ca^{+2}$/ME | 0.043 wt % | 0.086 wt % | 0.129 wt % | 0.258 wt % | 0.43 wt % |

Formulations 1.10-1.14 demonstrate varying water content in microemulsion. Formulations 1.15-1.19 demonstrate varying calcium concentration in the microemulsion.

Specific Examples 1.20-1.29—Doxorubicin-Loaded Nanoparticles

Doxorubicin-loaded nanoparticles were prepared similarly. Specifically, the microemulsion was formed as in Example 1.1, with surfactants-to-oil ratio of 88:12; doxorubicin, 4 mg, as 0.8 mL of aqueous solution with concentration 5 mg/mL, was added into the aqueous polymer solution, to yield a final microemulsion concentration of 400 μg/mL, and stirred at 1200 rpm for 10 minutes, until clear solution was obtained. The pH was adjusted to 7.5 with about 40 μL of 0.5% wt triethanolamine solution in water. Thereafter the aqueous phase was added into the oil, as in the Example 1.1, to form the microemulsion. Crosslinking was performed as in Example 1.1, stirring at 1200 rpm and adding the crosslinker solution using a syringe pump (NE 1000, New Era Pump Systems, NY) at the same rate 0.3 mL/min.

Formulation parameters are summarized in the table 4 below. C pol is concentration of the polymer in the microemulsion, $Ca^{+2}$/pol is the ratio between the crosslinking ion and the polymer, XL T is the crosslinking temperature, AqC is aqueous content in the microemulsion, DOX is doxorubicin concentration as μg/mL, and NP is the resulting nanoparticle size in nanometers.

TABLE 4

|  | C pol. (%) | $Ca^{+2}$/pol. | XL T | AqC | DOX | NP |
|---|---|---|---|---|---|---|
| 1.6 | 0.01 | 3:10 | 25° C. | 16 | 0 | 190.8 |
| 1.20 | 0.01 | 1:10 | 25° C. | 16 | 41.7 | 228.7 |
| 1.21 | 0.01 | 3:10 | 25° C. | 16 | 40.5 | 233.1 |
| 1.22 | 0.01 | 5:10 | 25° C. | 16 | 42.1 | 219.4 |
| 1.23 | 0.01 | 1:1 | 25° C. | 16 | 34.6 | 245.6 |
| 1.24 | 0.02 | 3:10 | 25° C. | 16 | 35.2 | 225.3 |
| 1.25 | 0.04 | 3:10 | 25° C. | 16 | 34.8 | 226.1 |
| 1.26 | 0.01 | 3:10 | 25° C. | 20 | 34.4 | 239.9 |
| 1.27 | 0.01 | 3:10 | 25° C. | 25 | 35.5 | 165.0 |
| 1.28 | 0.01 | 3:10 | 30° C. | 16 | 36.3 | 242.5 |
| 1.29 | 0.01 | 3:10 | 35° C. | 16 | 35.0 | 194.5* |

Formulations 1.20-1.23 demonstrate several calcium gluconate concentrations in the microemulsion (16% w/w of total aqueous phase, and 0.01% polymer concentration were kept constant) at the following $Ca^{++}$ ions/polymer ratios: 1:10, 3:10, 1:2, and 1:1. Formulations 1.24-1.25 demonstrate additional polymer concentrations, 0.02, and 0.04% wt, with the $Ca^{++}$ ions/polymer ratio of 3:10 and the microemulsion aqueous phase 16%. Formulations 1.26-1.27 demonstrate additional aqueous concentrations, 20% and 25%. Formulations 1.28-1.29 demonstrate composition 1.26 with different crosslinking temperatures, 30° C. and 35° C.

Specific Examples 1.30-1.37—Curcumin-Loaded Nanoparticles

Curcumin-loaded nanoparticles were prepared similarly to doxorubicin nanoparticles. Specifically, the microemulsion was formed as in Example 1.1 with surfactants-to-oil ratio of 90:10, and curcumin, 200 mg, was added into the formed microemulsion to final concentration 2.1% wt, and stirred at 500 rpm for 10 minutes, until clear solution was obtained. No further pH adjustment was performed. Crosslinking was performed as in Example 1.1, stirring at 1200 rpm and adding the crosslinker solution using a syringe pump (NE 1000, New Era Pump Systems, NY) at the same rate 0.3 mL/min. Temperature was controlled with a heat bath set to 35° C.

The formulations 1.30-1.37 are based on 1.2-1.9, with curcumin added as described and surfactants-to-oil ratio adapted to 90:10.

The specific formulations of the examples described can be readily obtained from the specific features as exemplified herein.

Example 2. Characterization of the Nanoparticles 2.1. Microscopic Observations

The Carbopol 974P NF polymer or carbomer homopolymer type B (USP/NF; carboxypolymethylene) is a high molecular weight polymer of acrylic acid cross-linked with allylpentaerythritol. Since it contains 56%-68% of free carboxylic acid groups, it can be further crosslinked by calcium ions at alkaline pH and precipitated. Referring now to FIG. 2, morphology of NPs as observed under the transmission electron microscope (TEM) and scanning electron microscope (SEM) are demonstrated. Photographs (A) and (B) are transmission electron microscopic (TEM) images of CHL-loaded (magnification ×8000) and unloaded NPs (magnification ×15000), respectively. Photograph (C) is a scanning electron microscopic image of loaded NPs (magnification ×200000). According to TEM analysis (FIGS. 2A and 2B), unloaded NPs are smaller (77-180 nm in diameter) than CHL-loaded NPs (200-40 nm in diameter). The dependency of NPs size on drug-loading can be explained by (a) increase of microemulsion nanodroplets in presence of CHL, resulting in larger NPs after crosslinking, and/or (b) decrease in the crosslinking process due to intercalation of the drug between the polymer chains. Although TEM analysis is accurate and reliable, it inspects only a limited subset of the entire sample, which may theoretically be a non-representative sample. In addition, the size difference between loaded and unloaded NPs may be obtained due to the drying technique during sample preparation. The unloaded nanoparticles may shrink during the drying process, while shrinking of CHL-loaded NP may be limited by drug occupying the pores and channels. In addition to the NP size, FIGS. 2A and 2B have shown that the unloaded NPs adopted a spherical shape with a smooth surface, while the loaded NPs were surrounded by a roughened surface. To understand the character of this granular structure, loaded NPs were further analyzed by SEM (FIG. 2C), which has clearly demonstrated a roughened structure. Though this interesting surface morphology is clearly related to drug incorporation within the polymeric network, its structure is still remaining to be investigated.

2.2. Influence of Calcium Ions Levels

Figure 3A:
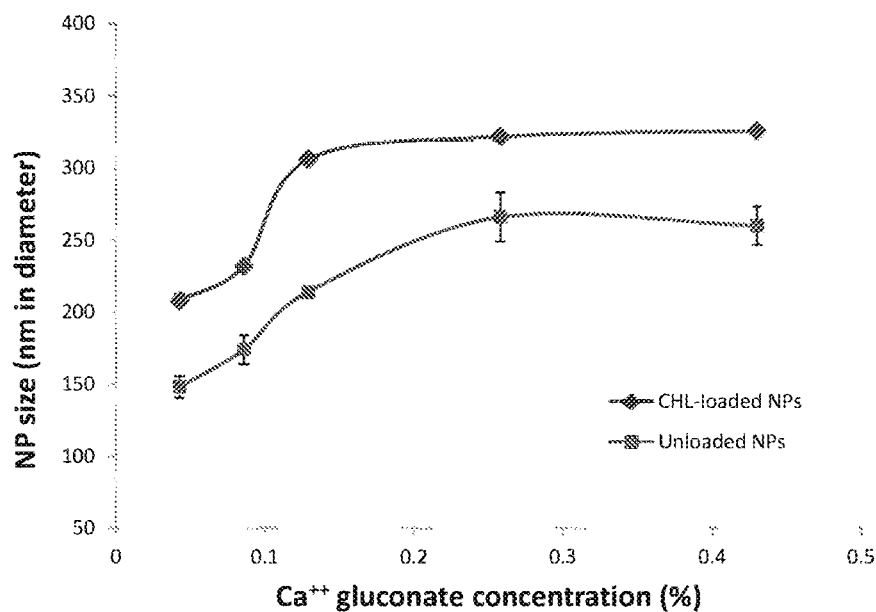
Figure 3B:
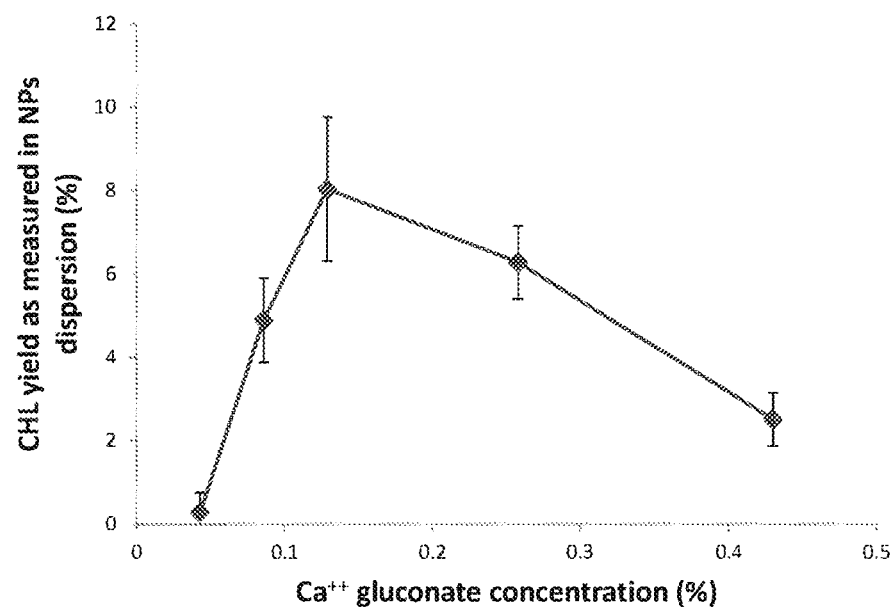

The nanoparticle size as measured by DLS was first evaluated in a series of five NP dispersions produced with various concentrations of calcium gluconate. The microemulsion used for these preparations contained 0.01% Carbopol and 30% aqueous phase. Referring now to FIGS. 3A and 3B, exemplified is the effect of $Ca^{+2}$ gluconate level on average particle size (in diameter) of CHL-loaded and unloaded NPs (A) and on CHL NP obtained in the NP dispersion after salting out and separation from the microemulsion (B). The aqueous phase in microemulsion was 30% and polymer concentration was 0.01% (w/w). It can clearly be seen in FIG. 3A that the average size of drug-loaded NPs was consistently larger than that the size of unloaded NPs. The influence of drug uploading on the NP size was in agreement with the abovementioned microscopic observation. The results have also demonstrated that increase in $Ca^{+2}$ concentrations in the microemulsion resulted in increase in NP size. With respect to the influence of drug uploading, it has been shown (FIG. 3A) that NP size reached to maximum after addition of 0.13% $Ca^{+2}$ gluconate to CHL-containing microemulsion while the maximal increase in the size of unloaded NPs required 0.26% $Ca^{+2}$ gluconate. Without being bound by a theory, yet in accordance with the TEM observation previously discussed, this phenomenon may indicate a decrease in the crosslinking reaction capability due to intercalation of the drug between the polymer chains, which may also result in size increase by surface interaction and aggregation. The percent yield of drug loading in the NP dispersion as a function of $Ca^{+2}$ gluconate concentrations is presented in FIG. 3B. As in the data regarding NP size, CHL loading in NP dispersion increased by elevating $Ca^{+2}$ levels and reached to maximum after addition of 0.13% $Ca^{+2}$ gluconate to CHL-containing microemulsion. Further elevation of $Ca^{+2}$ caused to a gradual decrease in drug loading capacity, which may indicate that reaction of the polymer with more $Ca^{+2}$ resulted in displacement of the drug out of the NPs.

2.3. Influence of the Aqueous Phase Content in Microemulsions

The NP size (as measured by DLS) was also evaluated in a series of five formulations containing various contents of aqueous phase, specifically, along dilution line DL20. In this experiment, the concentrations of the polymer and calcium gluconate were kept constant at 0.01% and 0.086%, respectively.

Figure 4:
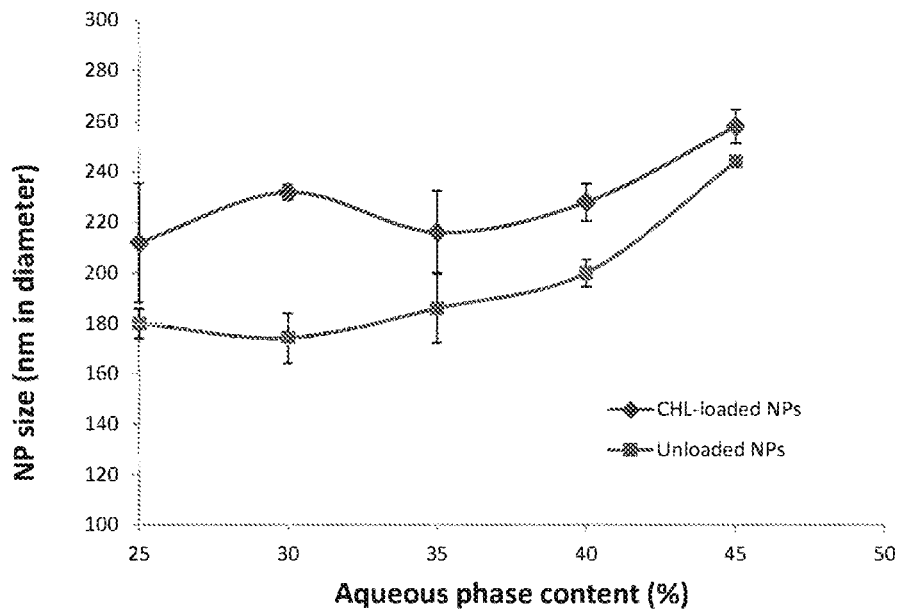

Referring now to FIG. 4, the effect of aqueous phase content of the microemulsion on the average size (in diameter) of CHL-loaded and unloaded NPs is demonstrated. The concentrations of the polymer and calcium gluconate were kept constant at 0.01% and 0.086%, respectively. Increase in NP size was effective only above 35% of water content (FIG. 4). Although the polymer and the cross-linking agent contents were kept constant in the microemulsion, their concentrations in the inner aqueous droplets decreased with increasing water content. The low concentrations of the reactants in the aqueous phase resulted in loose, swollen and larger NPs. The aqueous nanodroplets can also increase in size in microemulsions containing larger water phase, however, the size of the droplets are around 10 nm in diameter and only incremental changes occur in microemulsions containing more water. It is only reasonable, therefore, that these small changes in the nano-droplet size should not affect NPs whose size is between 200-300 nm.

Similarly to the results in FIG. 3A, FIG. 4 demonstrates the significant effect of CHL on NP size.

Figure 5:
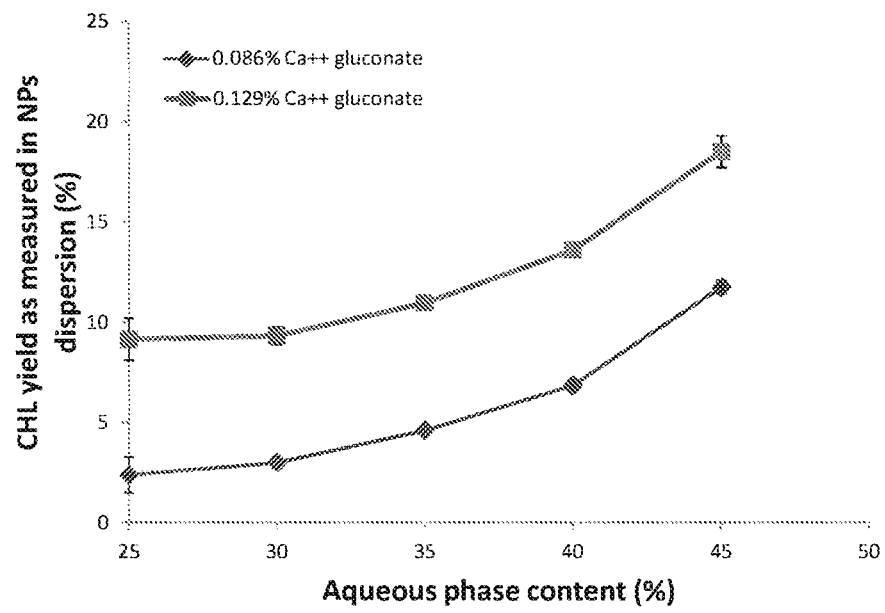

Referring now to FIG. 5, the effect of aqueous phase content of the microemulsion on CHL loaded in the NP dispersion produced by 0.086% and 0.129% Ca++ gluconate concentrations is exemplified. Polymer concentration was 0.01% (w/w). FIG. 5 presents the drug loading in the NP dispersions, which were produced by using two levels of $Ca^{+2}$ at various water concentrations in the microemulsion precursor. As shown, more CHL was loaded in NPs of formulations containing 0.13% calcium gluconate than NPs formed at 0.068% concentration, which is in good agreement with the data shown in FIG. 3B. FIG. 5 also shows that in formulations containing both $Ca^{+2}$ concentrations the drug loading capacity of NPs increased proportionally to the increase in water content. The extent of the increase in CHL loading was more significant when the aqueous phase was larger than 40% of the microemulsion. In light of the data presented in FIGS. 4 and 5, it may be concluded therefore that more drug can be entrapped in larger NPs than relatively small-size NPs. It should be noted that because the polymer content is kept constant in all formulations, dispersions of large NPs containing less NP units per volume and less surface area for drug diffusion than dispersions of small-size NPs. These parameters have been estimated in the modeling section below.

In conclusion of the characterization of NPs produced by the present process, NP dispersion formed after salting out of a microemulsion template containing 25% aqueous phase, 0.01% Carbopol polymer concentration, and 0.086% of calcium gluconate was found to be optimum in regard to particle size (200-300 nm) and drug loading.

Example 3. Drug Release and Modeling 3.1. Calculation of k' for Chloramphenicol

The apparent dialysis bag permeability constant (k') was calculated according to the method described in 'Materials and Methods' section 2.6.

Figure 6A:
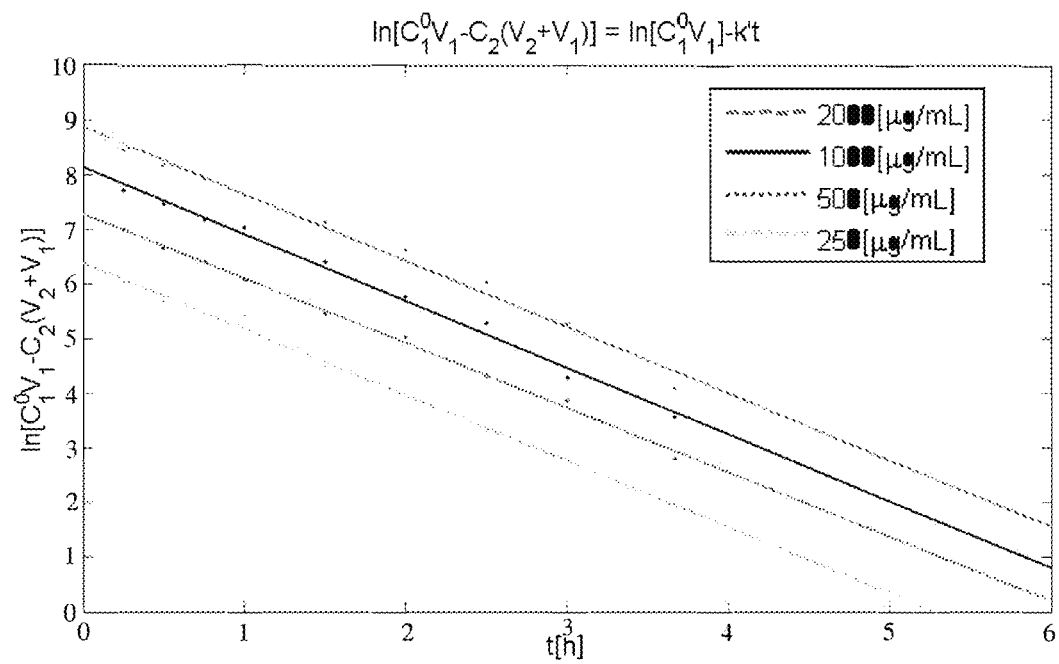
Figure 6B:
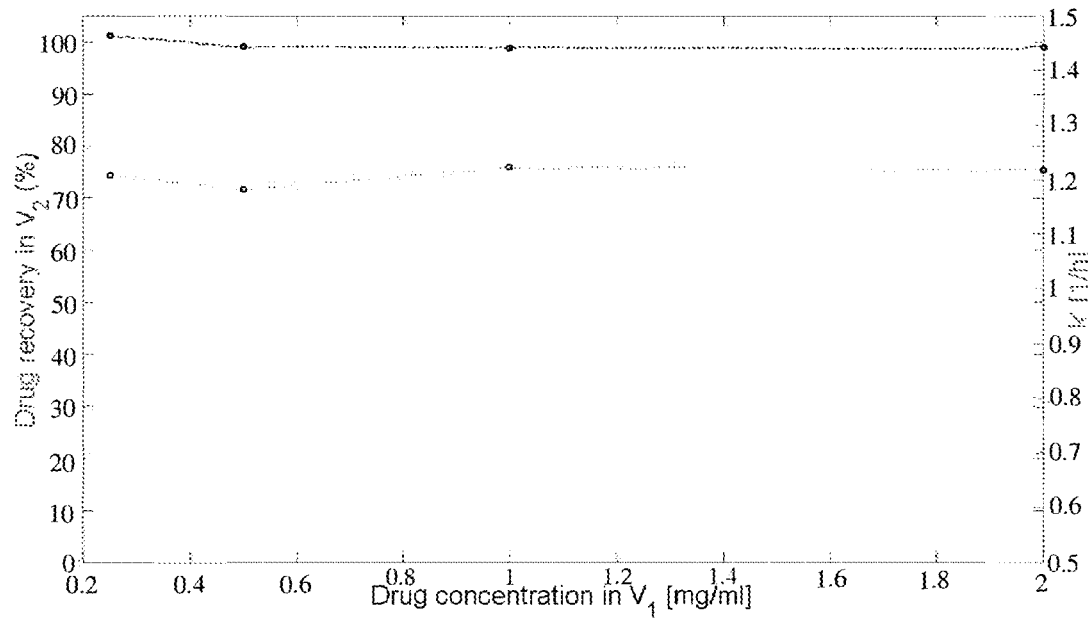

Referring now to FIGS. 6A and 6B, exemplified is (A) a plot of $\ln[C\_1\char`\^0 V\_1-C\_2(t)(V\_2+V\_1)]$ vs dialysis time of four different concentrations of chloramphenicol in NaCl 0.9% w/v; and (B) chloramphenicol recovery and the apparent permeability constant (k') values obtained from dialysis of various chloramphenicol concentrations in NaCl 0.9% w/v (V_1: donor solution, V_2: receiver solution). The equilibrium between the donor and the receiver solution was accomplished after about 4 hours for all samples. The values of the apparent permeability constant (k') were determined from the slope of the straight lines ($R^2=0.99$) obtained from the equation on top of FIG. 6A. As it shown in FIG. 6B, the calculated value of the apparent permeability constant (k'=1.207±0.018 $h^{-1}$) was negligibly affected by the initial drug concentration. In addition to the k' determination, this experiment examined the suitability of the dynamic dialysis technique for drug release testing from NPs. Based on these results, which have shown a total recovery of the drug in the receiver medium for all samples (FIG. 6B), the dynamic dialysis method was found as an appropriate technique for drug release evaluation of CHL-NPs.

3.2. Chloramphenicol Release from NPs

Figure 7:
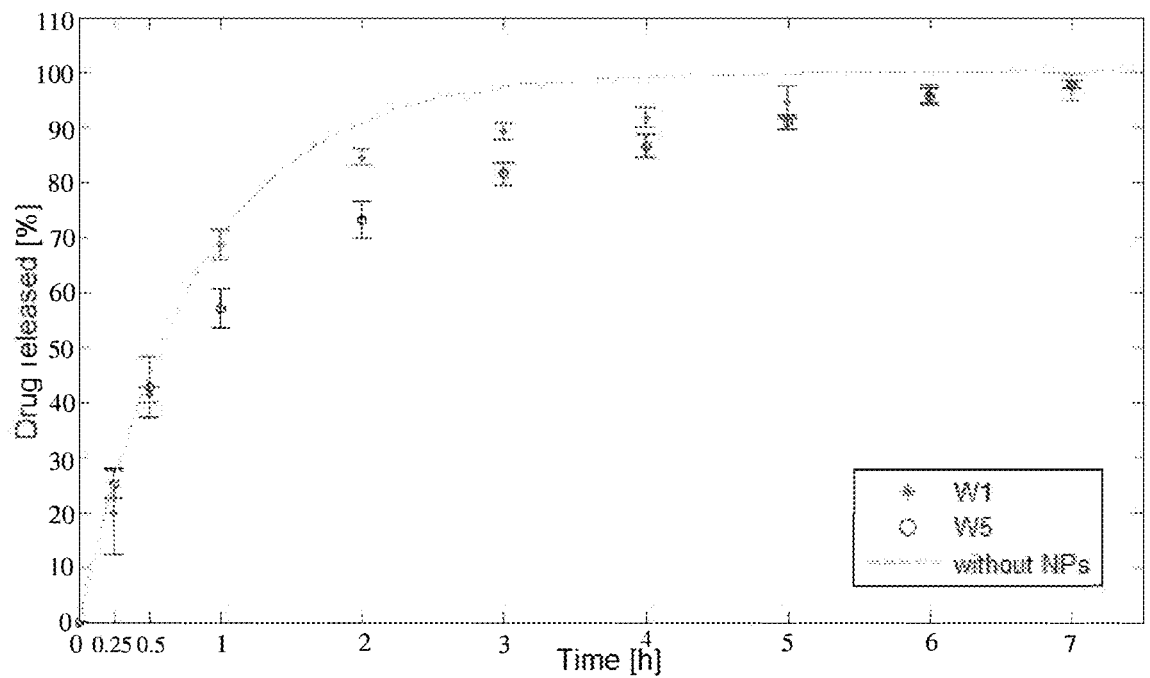

As discussed previously, drug release from NPs may be affected by the levels of drug loading. Therefore, two types of differently drug-loaded NPs were tested in order to characterize the mechanism. Both types of nanoparticles were prepared using 0.086% calcium gluconate and 0.01% Carbopol polymer, however, one formulation (formulation 1.10) was containing 25% aqueous phase and the other (formulation 1.14) 45% aqueous phase. Referring now to FIG. 7, the results are shown therein. The formulation 1.10 with 25% of aqueous phase is represented by empty diamonds (◇), designated W1, whereas the 1.14 with 45% of aqueous phase is a closed circle (o), designated W5.

Without being bound by a theory, the drug release of 1.10 may be attributed to matrix containing dissolved drug only, indicating that the drug concentration in the particles is lower or equal the solubility in the extraction medium (saline). The drug release of 1.14 may be attributed to larger amounts of drug entrapped in the nanoparticles, therefore the matrix may contain the dispersed drug, i.e. the concentration of the drug in the particle is above the solubility in the extraction medium. The assumptions may be corroborated by suitable calculations.

Example 4. Production and Use of Nanoparticles Comprising Curcumin or Doxorubicin Spherical nanoparticles (NPs) loaded with curcumin and doxorubicin have been prepared and characterized as disclosed herein. The overall manufacturing process (microemulsion preparation as a platform, polymer crosslinking, salting-out, extrusion and lyophilization) was optimized, evaluated and standardized for nanoparticle sizes (<200 nm), drug content, entrapment efficiency and minimal passive release. In addition, evaluation of the efficacy of anticancer drug loaded-NPs has begun using MCF-7 cell line of breast cancer, indicating advantageous activity of our product over anticancer drugs in plain solutions.

4.1. Optimizing the Formulation Parameters of Curcumin Nanoparticles

Figure 8A:
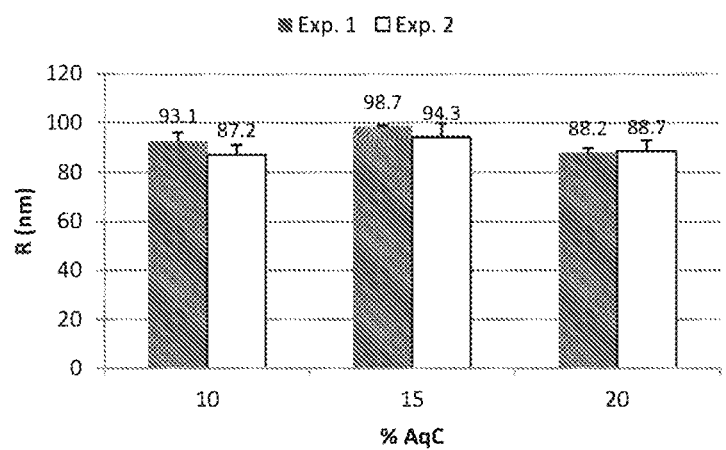
Figure 8B:
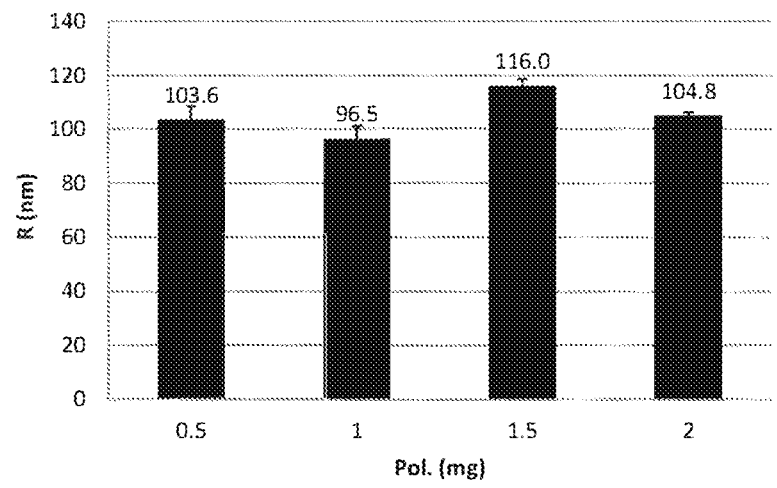
Figure 8C:
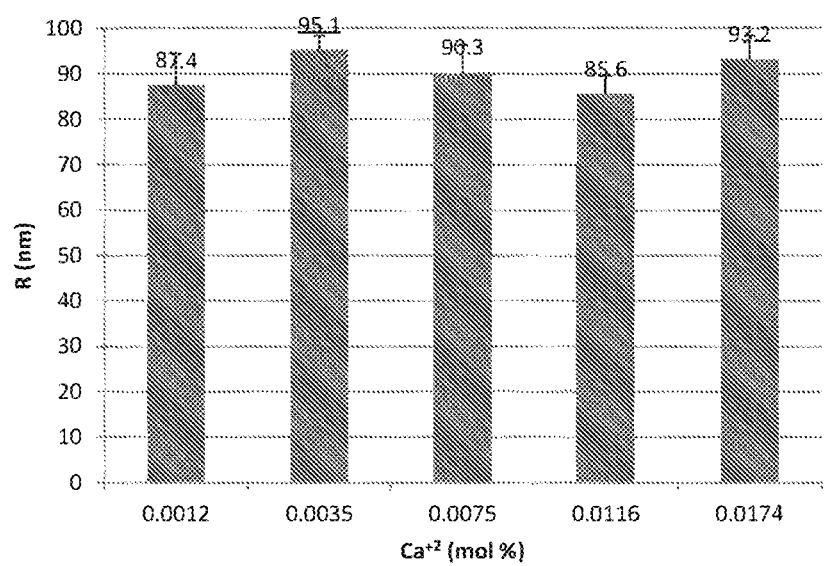

Several parameters were altered to characterize the formed nanoparticles. The goal was to achieve a narrow range of size distribution having diameters between 100-200 nm. The parameters that were changed were the content of aqueous phase in the microemulsion (ME) precursor, polymer quantity, and the cross-linker concentrations. Referring now to FIGS. 8A-8C, the dependence between the nanoparticle radius (R, given in nm) and the aqueous content, designated "AqC" (8A), amount of polymer, designated "Pol." (8B), and the amount of cross-linker, expressed in molar percent, designated "$Ca^{+2}$" (8C) is exemplified. FIG. 8A demonstrates formulations with different percentages of aqueous phase content in ME (10%, 15%, 20% w/w) were prepared and their nanoparticles size were analyzed. It should be noted that in this series of formulations, the polymer quantity (but not its concentrations in the aqueous phase) as well as the cross-linker level were kept constant. The second set of formulations was prepared with different quantities of the polymer. The results of this experiment are shown in FIG. 8B. The mean particle radius is shown versus the amount of polymer (Pol.), expressed in mg per 10-mL formulation. In the third set of experiments (FIG. 8C), different levels of the cross-linker (0.0012, 0.0035, 0.0075, 0.0116, 0.0174 mol % of $Ca^{+2}$ ions) were investigated. The polymer content (10 mg %) and the aqueous phase percentage (25%) were kept constant.

4.2. Nanoparticle Morphology—Curcumin

Figure 9A:
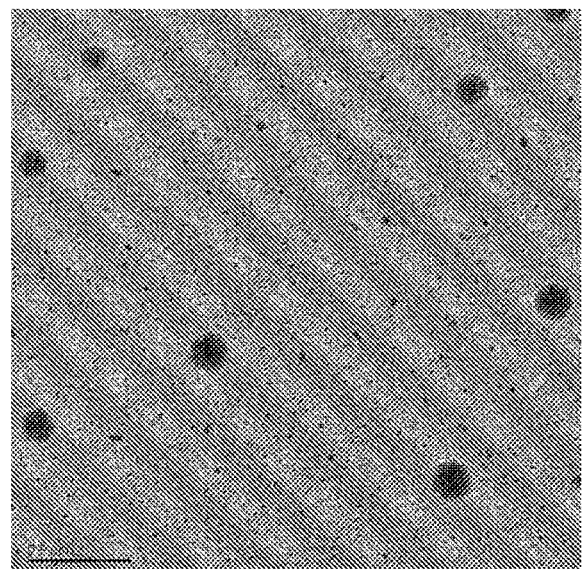
Figure 9B:
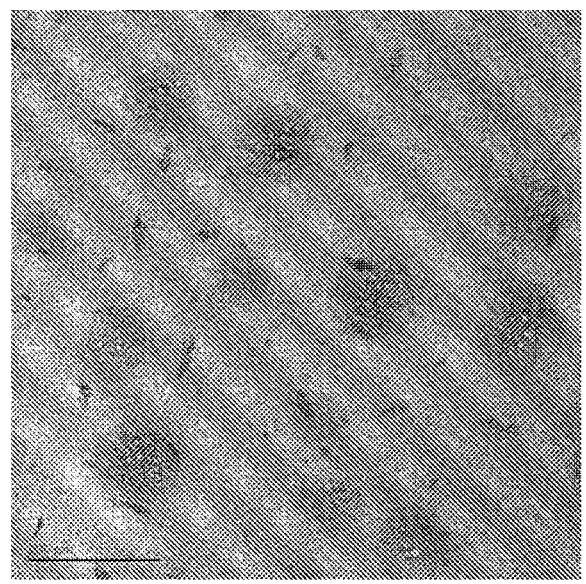

The shape of the nanoparticles was inspected by transmission electron microscopy (TEM). Referring now to FIGS. 9A and 9B, TEM images of nanoparticles loaded with curcumin are exemplified.

4.3. Drug Loading—Curcumin

Figure 10:
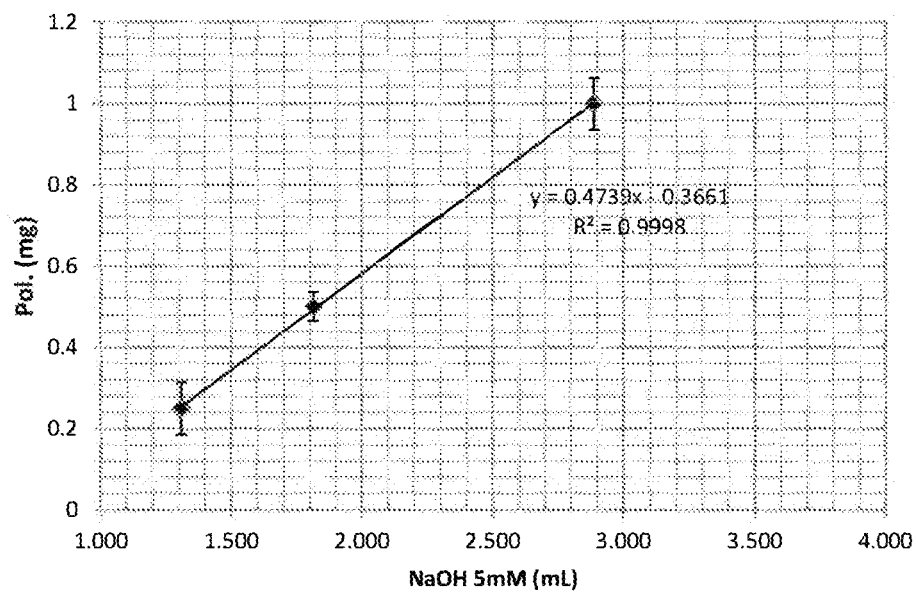

Referring now to FIG. 10, the reference curve obtained by potentiometric titration of three different polymer amounts is exemplified, from pH 4.5 to 9.0. The amount of polymer in the solution, designated as "Pol.", is correlated with the amount of sodium hydroxide 5 mM solution required for the titration. By this assay the yield of the polymer in the process and its quantity in the nanoparticles are determined. Table 5 below shows the results of the drug loading tests.

TABLE 5

Analytical summary of curcumin loading on NPs

| | | |
|---|---|---|
| Calcium gluconate concentration (% w/v) | 0.645% | 1.0% |
| X-linker added (mole) | 7.5E–06 | 11.6E–06 |
| X-linker in pre-lyophilized product (mole) | 8E–07 (SD: ±1E–07) | 1.16E–06 (SD: ±6E–08) |
| Polymer conc. (mg/mL) | 0.15 (SD: ±0.03) | 0.15 (SD: ±0.03) |
| Curcumin concentration in NPs (µg/mL) | 34.47 (SD: ±0.15) | 72.5 (SD: ±1.7) |
| Curcumin Loading (w [CUR]/w [Polymer]) | 0.230 (SD: ±1E–03) | 0.48 (SD: ±0.01) |

4.4. Drug Release—Curcumin

Figure 11:
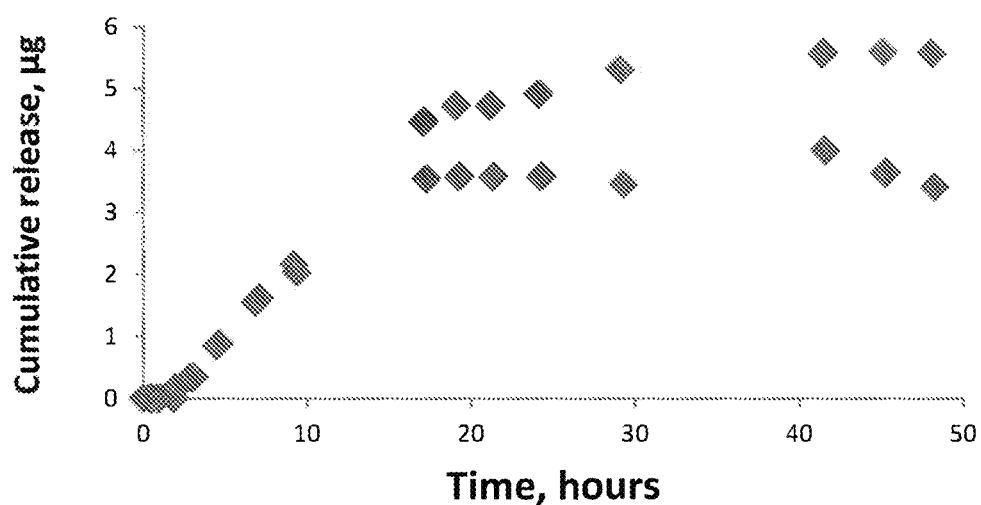

The release behavior of curcumin from hydrogel nanoparticles with drug loading of 0.48 w/w was determined at 37° C. at pH 7 with in BSA (2% w/v) and NaCl (0.9% w/v) added to the dissolution medium. The results are shown in the FIG. 11. The release test was done on two different production batches and lasted about 48 hours. It should be noted that the percentage of curcumin release from nanoparticles was found to be between 6-7% during the first 24 hours, indicating that a second phase of slower release rate takes place.

4.5. Drug Loading—Doxorubicin

Four batches of the doxorubicin-loaded product were produced according described above. Previously, several attempts to load the drug had revealed that pH adjustment was critical for NPs formation. The salting-out technique was not changed; however, the dissolution of DOX-HCl was carried out within the preparation of the polymer solution (i.e., DOX was not introduced directly in microemulsion), pH was adjusted and then microemulsion was spontaneously formed by mixing with the oily phase. Particle size was determined to be 100 nm in diameter.

4.6. Drug Release—Doxorubicin

The release of DOX from NPs was evaluated by incubating the DOX-NP dispersion at 37° C. in the donor compartment of a Franz diffusion cell system (PermeGear, Inc., Hellertown, Pa.). The diffusion area was 1.767 cm$^2$ (15 mm diameter orifice), and the receiver compartment volume was 12 mL. The solutions in the water-jacketed cells were thermostated at 37° C. and stirred by externally driven, Teflon-coated magnetic bars. A synthetic membrane (Snake-Skin Dialysis Tubing, 10,000 MW cutoff, 22 mm, Thermo Fisher Scientific, Rockford, USA) was cut and placed on the receiver chambers and the donor chambers were then clamped in place. The receiver chamber was filled with phosphate buffered saline (PBS, pH 7.4). Aliquots (0.5 mL each) of DOX-NP dispersion or plain DOX solutions in water were applied over the membrane. Samples (1 mL) were withdrawn from the receiver solution at predetermined time intervals, and the receiver cell was replenished up to its marked volume with fresh buffer solution each time. Addition of PBS to the receiver compartment was performed with great care to avoid trapping air beneath the membrane. The receiver samples were taken into 1.5-mL vials and kept at −20° C. until analyzed by HPLC.

Figure 12A:
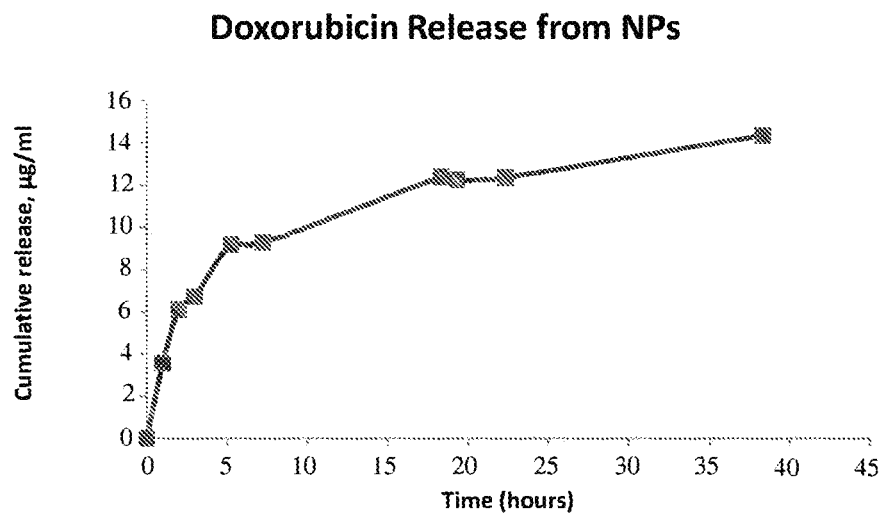
Figure 12B:
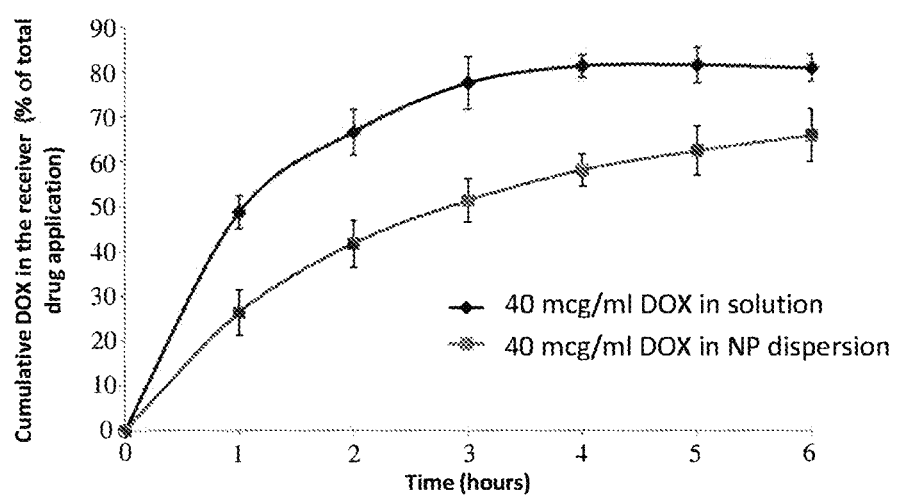

The release of doxorubicin was shown to be time dependent over two days and even may be longer. The graphs of cumulative release of doxorubicin are exemplified in the FIGS. 12A and 12B.

4.7. Cytotoxic Studies—MCF7 Cell Line

Figure 13A:
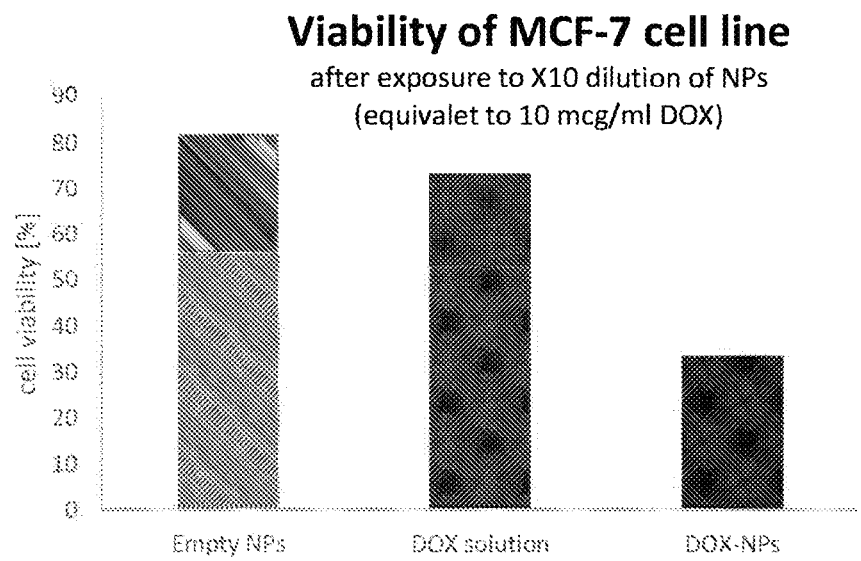
Figure 13B:
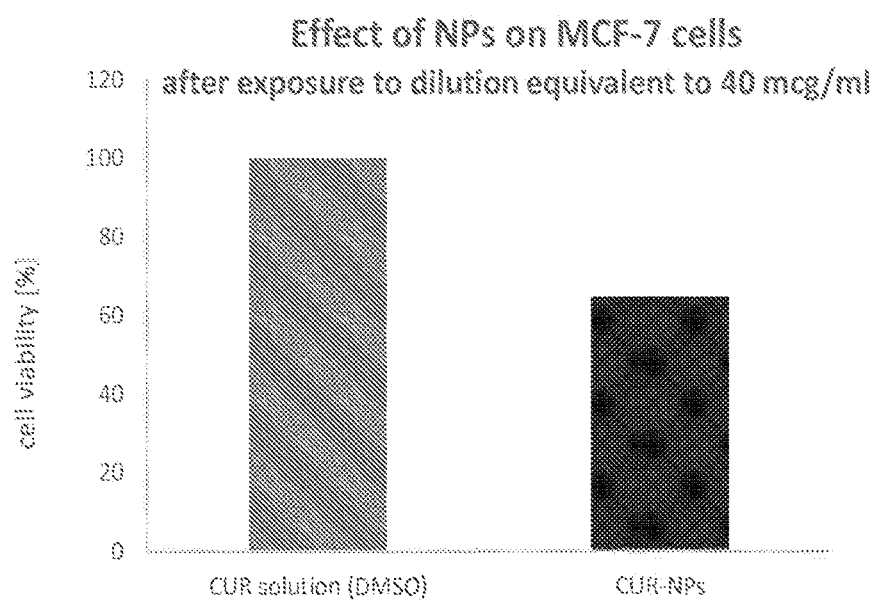
Figure 13C:
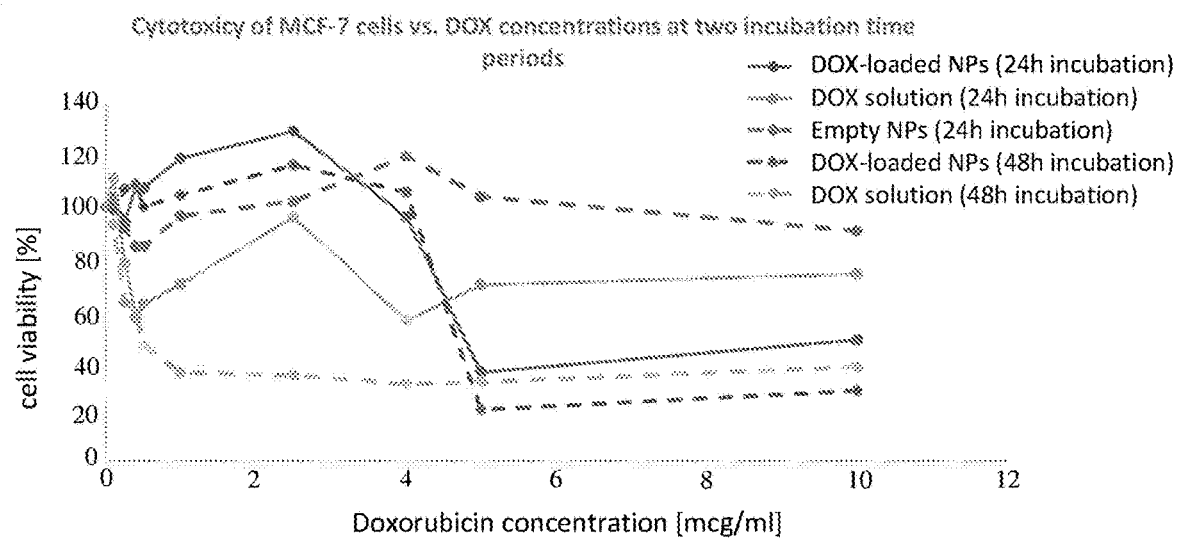

The direct effect of curcumin and doxorubicin on the viability of cultured cells was assessed in vitro using the MCF-7 cells (cell line of breast cancer). The cells (1×10$^4$) were plated in 96-well plates and were allowed to attach for 24 h at 37° C. in a 5% $CO_2$ humidified atmosphere. Fresh cell medium was then prepared with test compounds in appropriate dilutions (equivalent to their concentrations as determined by HPLC). Cell growth after 48 h was assayed by MTT assay [3-(4,5-Dimethylthiazol-2-yl)-2,5-diphenyltetrazolium bromide, Sigma-Aldrich] and was evaluated by measuring the absorbance at 540 nm after 3 h of incubation in a medium containing 0.5 mg/ml MTT (Sunrise™ absorbance plate reader, TECAN). Referring now to FIGS. 13A-13C, the figures demonstrate the current results, indicating that NPs loaded with anticancer drugs are more efficacious than the drugs in plain solutions. FIG. 13A shows that DOX-loaded NPs are more cytotoxic than DOX in plain solution (24 h incubation). FIG. 13B demonstrates the same phenomenon with curcumin. FIG. 13C presents dose response behavior of DOX-loaded and unloaded NPs vs. solutions at various concentrations after 24-h and 48-h incubation. It could be noted that due to the slow release manner of the drug from NPs, the effect of the NPs is expressed only from minimum 4-5 mg/ml, compared with the solution which is highly cytotoxic at 1 mg/ml.

4.8. Animal Study

Female C57BL/6 mice (5-6 weeks old, 14-18 g) were obtained from Harlan Laboratories Ltd (Jerusalem, Israel). Mice were housed under humidity- and temperature-controlled conditions, and the light/dark cycle was set at 12-h intervals. The animal protocol was reviewed and approved by the Ben Gurion University of the Negev Institutional Committee for the Ethical Care and Use of Animals in Research, which complies with the Israeli Animal Welfare Law.

B16F0 melanoma cells were maintained in RPMI 1640 medium supplemented with 10% bovine serum and 200 µM L-glutamine, 10 units/mL penicillin, and 10 µg/mL streptomycin (Biological Industries, Beth Ha'Emek, Israel). The cells were kept at 37° C. in a 5% $CO_2$ humidified atmosphere.

The mice were inoculated with melanoma B16F0 cells (1×10$^6$) subcutaneously in the right flank of the mice. After tumors had been visualized a week later, the mice were weighed and measured for tumor size (244±213 mm$^3$), and were randomly sorted into three groups. The groups were assigned for untreated control animals, treated animals with DOX-HCl solution (40 µg/ml, 0.2 mL/animal), and treated animals with DOX-NP dispersion (40 µg/ml, 0.2 mL/animal) (n=12 mice/group, n=11 mice in the control group). The dose of DOX administered to the treatment groups was 0.5 mg/kg twice a week, by subcutaneous (s.c.) injection 1-cm proximal to the tumor at the frontal side. B-16 melanoma is an aggressive skin tumor that is not typically treated with doxorubicin, therefore s.c. administration of the anticancer drug has been thought to be more effective than the i.p. injection which is widely-used in xenograft tumor models. Tumor volumes and mouse body weights were measured routinely before each treatment. Measurement of tumor size was performed with a caliper in two dimensions, and individual tumor volumes (V) were calculated by the formula: V=[length×(width)$^2$]×π/6.

The statistical differences between the release data obtained from the various formulations were analyzed employing the two-way unweighted means analysis of variance (ANOVA) test. The statistical differences between the therapeutic effects of different treatments on tumor growth were determined by two-tailed Student's test. The differences among groups were considered significant when p values <0.05.

Figure 14A:
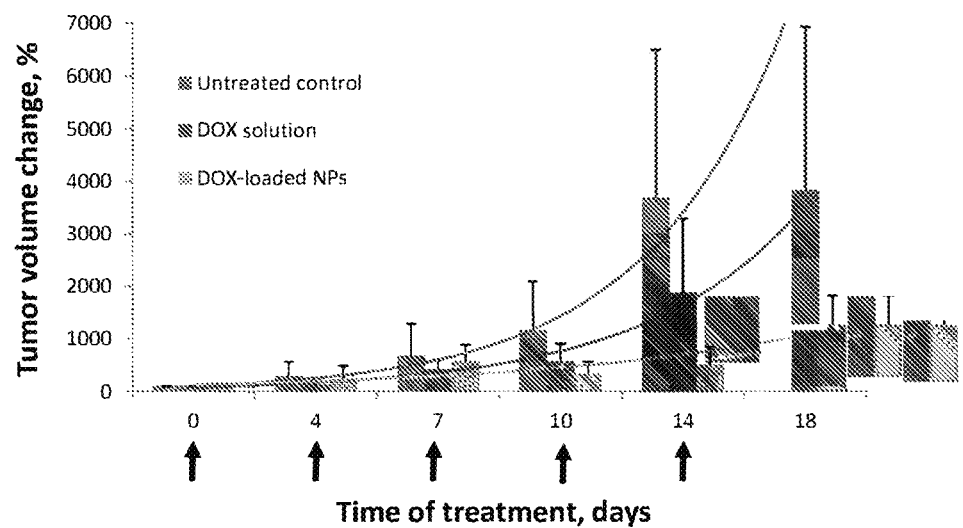
Figure 14B:
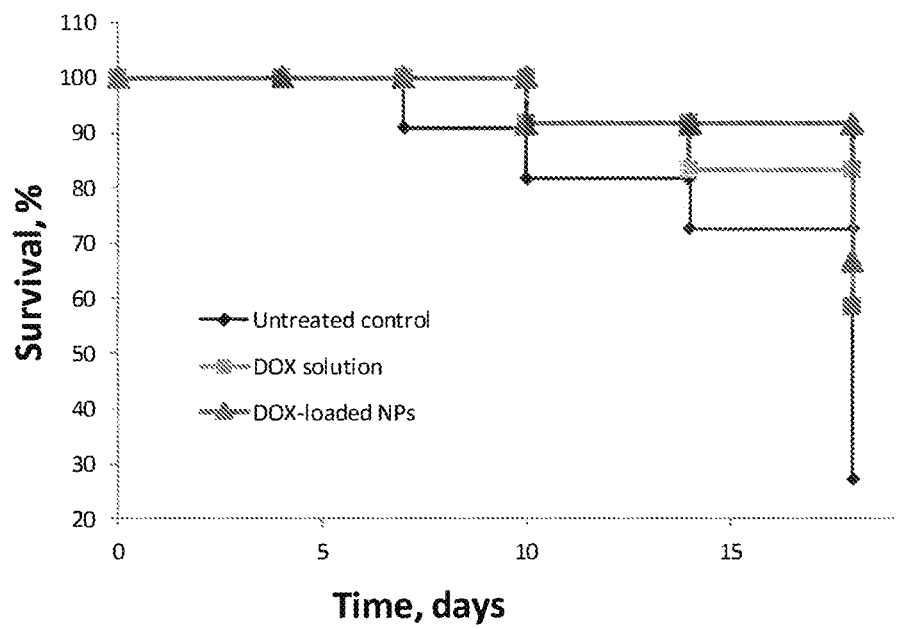

Referring to FIG. 14A, the tumor growth inhibition by the chemotherapeutic drug in terms of volume change during the course of treatment (18 days) is shown. A comparison between drug-induced inhibition and untreated control is presented. It is readily seen that most pronounced tumor growth inhibition was observed in mice treated with DOX-NPs. Compared with 40 µg/ml DOX-HCl solution treatment twice a week, the same dosage of DOX-loaded NPs dramatically reduced tumor growth (Student t-test, p<<0.05). The significant inhibition of tumor growth by DOX-NPs demonstrates the efficacy of NP encapsulation. Referring now to FIG. 14B, mortality occurred in the untreated group at 7 days (14 days after inoculation) and increased rapidly to 73% mortality (or 27% survival) at day 18. In comparison to the untreated control mice, treatment apparently increased animal survival. However, only one mouse of the twelve mice died in the group which received DOX-NPs after 14 days of treatment while three more died at day 18 (67% survival). This was compared to the treatment with DOX-HCl solution, which summed up with a relatively higher mortality and less survived animals (58% survival).

Example 5. Nanoparticles Preparation—A General Protocol

Figure 15:
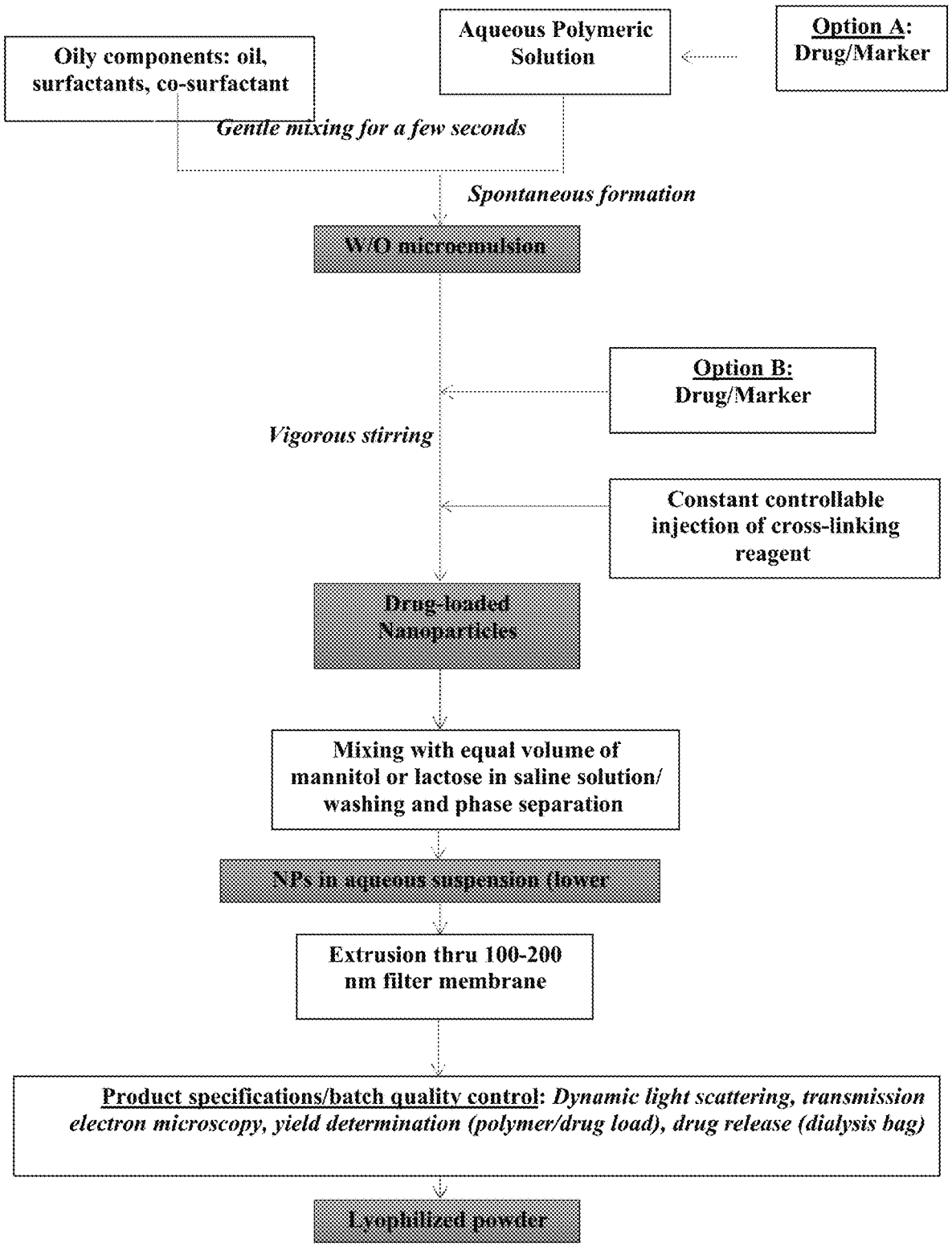

The method for producing nano-sized particles according to the present invention is schematically presented in the flow sheet shown in FIG. 15.

While the present disclosure has been illustrated and described with respect to a particular embodiment thereof, it should be appreciated by those of ordinary skill in the art that various modifications to this disclosure may be made without departing from the spirit and scope of the present disclosure.

REFERENCES

1. Remington, The Science and Practice of Pharmacy, A. R. Gennaro (ed.), 20th Edition, 2000.
2. K. Jarvinen, T. Jarvinen, A. Urtti, Ocular absorption following topical delivery, Adv. Drug Deliv. Rev. 16 (1995) 3-19.
3. Z. Pavelic, N. Skalko-Basnet, I. Jalsenjak, Liposomes containing drugs for treatment of vaginal infections, Europ. J. Pharm. Sci. 8 (1999) 345-351.
4. WHO News and Activities, Long-acting chloramphenicol for bacterial meningitis, Bull. World Health Organ. 71 (1993): 117-118, 123-125.
5. S. S. Wali, J. T. MacFarlane, W. R. L. Weiz, et al., Single injection treatment of meningococcal meningitis: long-acting chloramphenicol, Trans. R. Soc. Trop. Med. Hyg. 73 (1979) 698-701.
6. B. Pécoul, F. Varaine, M. Keita, G. Soga, A. Djibo, G. Soula, A. Abdou, J. Etienne, M. Rey, Long-acting chloramphenicol versus intravenous ampicillin for treatment of bacterial meningitis, Lancet 338 (1991) 862-866.
7. K. K. Halder, B. Mandal, M. C. Debnath, H. Bera, L. K. Ghosh, B. K. Gupta, Chloramphenicol-incorporated poly lactide-co-glycolide (PLGA) nanoparticles: formulation, characterization, technetium-99m labeling and biodistribution studies, J. Drug Target. 16 (2008) 311-320.
8. M. D. Chavanpatil, A. Khdair, J. Panyam, Surfactant-polymer nanoparticles: a novel platform for sustained and enhanced cellular delivery of water-soluble molecules, Pharm. Res. 24 (2007) 803-810.
9. M. Lee, Y. W. Cho, J. H. Park, H. Chung, S. Y. Jeong, K. Choi, D. H. Moon, S. Y. Kim, I.-S. Kim, I. C. Kwon, Size control of self-assembled nanoparticles by an emulsion/solvent evaporation method, Colloid Polym. Sci. 284 (2006) 506-512.
10. T. Govender, S. Stolnik, M. C. Garnett, L. Ilium, S. S. Davis, PLGA nanoparticles prepared by nanoprecipitation: drug loading and release studies of a water soluble drug, J. Control. Rel. 57 (1999) 171-185.
11. E. Allémann, J. C. Leroux, R. Gurny, E. Doelker, In vitro extended-release properties of drug-loaded poly(DL-lactic acid) nanoparticles produced by a salting-out procedure, Pharm. Res. 10 (1993) 1732-1737.
12. C. E. Astete, C. M. Sabliov, Synthesis and characterization of PLGA nanoparticles, J. Biomater. Sci. Polym. Ed. 17 (2006) 247-289.
13. P. Tewa-Tagne, S. Briancon, H. Fessi, Spray-dried microparticles containing polymeric nanocapsules: formulation aspects, liquid phase interactions and particles characteristics, Int. J. Pharm. 325 (2006) 63-74.
14. P. Tewa-Tagne, G. Degobert, S. Briancon, C. Bordes, J. Y. Gauvrit, P. Lanteri, H. Fessi, Spray-drying nanocapsules in presence of colloidal silica as drying auxiliary agent: formulation and process variables optimization using experimental designs, Pharm. Res. 24 (2007) 650-661.
15. C. H. Hsu, Z. Cui, R. J. Mumper, M. Jay, Preparation and characterization of novel coenzyme Q10 nanoparticles engineered from microemulsion precursors, AAPS PharmSciTech. 4 (2003) E32.
16. M. Trotta, M. Gallarate, M. E. Carlotti, S. Morel, Preparation of griseofulvin nanoparticles from water-dilutable microemulsions, Int. J. Pharm. 254 (2003) 235-242.
17. J.-O. You, C.-A. Peng, Calcium-alginate nanoparticles formed by reverse microemulsion as gene carriers, Macromol. Symp. 219 (2005) 147-153.
18. J. Nesamony, P. R. Singh, S. E. Nada, Z. A. Shah, W. M. Kolling, Calcium alginate nanoparticles synthesized through a novel interfacial cross-linking method as a potential protein drug delivery system, J. Pharm. Sci. 101 (2012) 2177-2184.
19. S. W. Provencher, CONTIN: a general purpose constrained regularization program for inverting noisy linear algebraic and integral equations, Comp. Phys. Commun. 27 (1982) 229-242.
20. P. K. Gupta, C. T. Hung and D. G. Perrier, Quantitation of the Release of Doxorubicin from Colloidal Dosage Forms Using Dynamic Dialysis, 1987, J. of Pharm. Sci. 76 (1987), 141-145.
21. Y. Zhou, X. Y. Wu, Modeling and analysis of dispersed-drug release into a finite medium from sphere ensembles with a boundary layer, J. Control. Rel., 90 (2003), 23-36.
22. B. V. N Nagavarma, K. S. Y. Hemant, A. Ayaz, L. S. Vasudha, H. G. Shivakumar, Different Techniques For Preparation Of Polymeric Nanoparticles—A Review, Asian J of Pharmaceutical and Clinical Research, 5 (2012), 16-23.

What is claimed is:

1. A nano-sized particle comprising a cross-linked polymer, wherein the polymer includes a carbomer that is a cross-linked polyacrylic acid homopolymer; wherein said polymer is cross-linked with a metal ion, wherein said polymer is further chemically cross-linked with a cross-linking moiety selected from the group consisting of allyl pentaerythritol, allyl sucrose, polyvinyl alcohol, divinyl glycol, and tetraethylene glycol, and wherein said nano-sized particle is pharmaceutically acceptable and having an essentially spherical shape, and a size of 50-500 nm, wherein the nano-sized particles are prepared by the salting out/phase reversal process with involvement of microemulsion and without organic solvent.

2. The particle according to claim 1, wherein the metal ion is selected from the group consisting of alkali earth metal ions, divalent transition metal ions, trivalent metal ions, and $Ag^+$.

3. The particle according to claim 1, further comprising at least one active agent selected from the group consisting of curcumin,-doxorubicin, and chloramphenicol.

4. The particle according to claim 1, wherein said polymer is poly(acrylic acid) cross-linked with allyl pentaerythritol or allyl sucrose, and wherein said metal ion is $Ca^{2+}$.

5. A composition comprising the nanosized particles according to claim 1 and a physiologically acceptable carrier, wherein said composition is a pharmaceutical composition or a cosmetic composition.

* * * * *